United States Patent
Encina et al.

(10) Patent No.: US 9,211,305 B2
(45) Date of Patent: Dec. 15, 2015

(54) PHARMACEUTICAL COMPOSITIONS WITH GLYCOSAMINOGLYCANS AND USE THEREOF IN THE TREATMENT OF CHRONIC ULCERS

(71) Applicant: LABORATORIOS FARMACEUTICOS ROVI S.A., Madrid (ES)

(72) Inventors: Ivan Lopez-Belmonte Encina, Madrid (ES); Maria De Los Angeles Canales Mayordomo, Madrid (ES); Elena Cebadera Miranda, Madrid (ES)

(73) Assignee: Laboratories Farmaceuticos Roui, S.A., Madrid (ES)

( * ) Notice: Subject to any disclaimer, the term of this patent is extended or adjusted under 35 U.S.C. 154(b) by 0 days.

(21) Appl. No.: 14/018,840

(22) Filed: Sep. 5, 2013

(65) Prior Publication Data
US 2014/0066402 A1 Mar. 6, 2014

Related U.S. Application Data

(62) Division of application No. 13/001,895, filed as application No. PCT/ES2009/070264 on Jun. 30, 2009, now abandoned.

(30) Foreign Application Priority Data

Jul. 1, 2008 (ES) .................................. 200802002

(51) Int. Cl.
| | |
|---|---|
| A61K 31/70 | (2006.01) |
| A61K 31/727 | (2006.01) |
| A61K 9/00 | (2006.01) |
| A61K 31/726 | (2006.01) |
| A61K 47/26 | (2006.01) |

(52) U.S. Cl.
CPC ............. *A61K 31/727* (2013.01); *A61K 9/0019* (2013.01); *A61K 31/726* (2013.01); *A61K 47/26* (2013.01)

(58) Field of Classification Search
CPC .......................... A61K 31/727; A61K 31/726
See application file for complete search history.

(56) References Cited

U.S. PATENT DOCUMENTS
| | | | |
|---|---|---|---|
| 4,652,555 A | 3/1987 | Goulay | |
| 5,236,910 A | 8/1993 | Egidio | |
| 6,569,840 B1 | 5/2003 | Yamashina | |
| 2006/0040896 A1 | 2/2006 | Kennedy | |

FOREIGN PATENT DOCUMENTS

EP 0513513 A1 11/1992

OTHER PUBLICATIONS

Kalani, M., et al., "Effect of Dalteparin on Healing of Chronic Foot Ulcers in Diabetic Patients With Peripheral Arterial Occlusive Disease," Diabetes Care, (Sep. 2003), vol. 26, No. 9, pp. 2575-2580.
Kalani, M., et al., "Beneficial effects of dalteparin on haemostatic function and local tissue oxygenation in patients with diabetes, sever vascular disease and foot ulcers," Thrombosis Research, (Feb. 2, 2007), vol. 120, pp. 653-661.
Jivegard, L., et al., "Effects of Three Months of Low Molecular Weight Heparin (dalteparin) Treatment After Bypass Surgery for Lower Limb Ischemia—A Randomised Placebo-controlled Double Blind Multicentre Trial," European Journal of Vascular and Endovascular Surgery, (2005), vol. 29, pp. 190-198.
International Search Report issued Dec. 10, 2009 in PCT/ES09/070264 filed Jun. 30, 2009.
Rozin, A.P. et al., "Recalcitrant leg ulcer due to mixed connective tissue disease", The Netherlands Journal of Medicine (Mar. 2006), vol. 64, No. 3, pp. 91-94.
Rullan, M et al., "Ensayo clinico, controlado con placebo, triple ciego, para evaluar la eficacia de una heparina de bajo peso molecular (bemiparina) en el tratamiento de las ulceras torpidas del pie diabetico, en atencion primaria", Aten Primaria, (Nov. 18, 2002), vol. 31, No. 8, pp. 539-544.
Planes, A., "Review on bemiparin sodium—a second generation low molecular weight heparin—and its applications in venous thromboembolism", Expert opinion, Pharmacother., (2003), 4, pp. 1551-1561.
L. Torkvist et al., "Low molecular weight heparin as adjuvant therapy in active ulcerative colitis", Aliment Pharmacol. Ther., (1999), vol. 13, No. 10, pp. 1323-1328.
Rullan, M., et al. "Úlceras del pie diabético y tratamiento con heparinas de bajo peso molecular", Medicina Clinica, (2002), vol. 118, No. 19, p. 757.
Rullan et al. ("Treatment of chronic diabetic foot ulcers with bemiparin: a randomized, triple-blind, placebo-controlled, clinical trial", in Diabetic Medicine (2008), 25, 1090-1095).
Aragon-Sanchez et al. ("Comments of the use of bemiparin in diabetic foot ulcers", in Diabetic Medicine (2009), 26, 110).
Eikelboom et al. ("Low Molecular Weight Heparins and Heparinoids"; MJA, (Oct. 2002), 177, 379-383).
Pfizer ("Study of the effects of Fragmin in the Treatment of Neuroischaemic Foot Ulcers in Diabetic Patients (FEENICS)"; www.clinicaltrials.gov, Clinical Trial No. NCT00662831, (Dec. 2011).

*Primary Examiner* — Elli Peselev
(74) *Attorney, Agent, or Firm* — Rick Matos; Innovar, L.L.C.

(57) ABSTRACT

The invention relates to a composition of glycosaminoglycans for the treatment of diabetic foot ulcer, it specifically relates to low molecular weight heparins (LMWHs) and very low molecular weight heparins (VLMWHs) in the treatment of chronic ulcers, particularly of diabetic foot ulcers, and more specifically in the manufacture of a medicinal product for the treatment of chronic ulcers, and particularly diabetic foot ulcers and pressure ulcers.

24 Claims, 13 Drawing Sheets

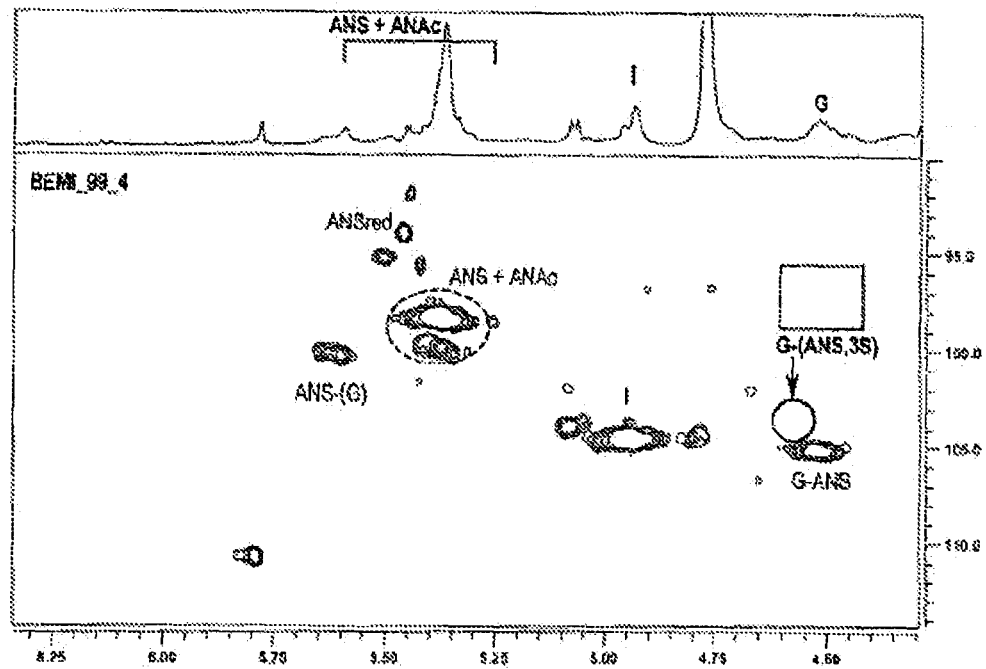
FIGURA 2G
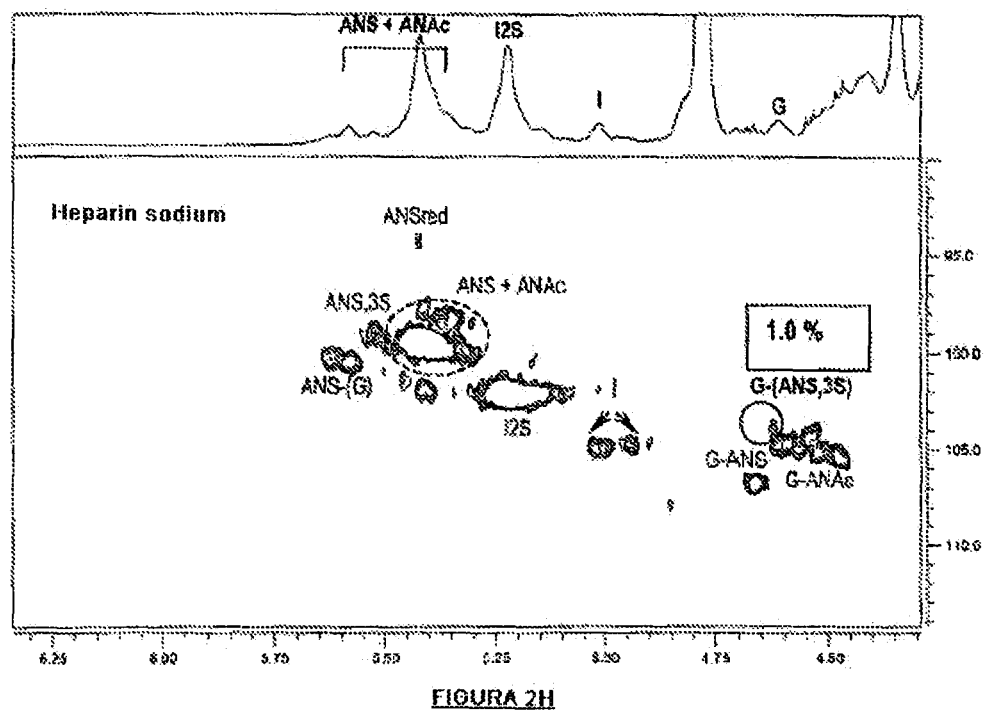
FIGURA 2H

R = COCH$_3$ or SO$_3^-$

| Loss of anti-Xa activity >95% |
| Loss of anti-Xa activity approx. 75% |
| Loss of anti-Xa activity approx. 50% |

PHARMACEUTICAL COMPOSITIONS WITH GLYCOSAMINOGLYCANS AND USE THEREOF IN THE TREATMENT OF CHRONIC ULCERS

CROSS-REFERENCE TO EARLIER FILED APPLICATIONS

The present application claims the benefit of U.S. Ser. No. 13/001,895 filed Dec. 29, 2010 and having a 371 filing date of Apr. 29, 2011, which is a 371 application of PCT/ES2009/070264 filed Jun. 30, 2009, which claims the benefit of Spanish Application No. P200802002 file Jul. 1, 2008, the entire disclosures of which are hereby incorporated by reference.

FIELD OF THE INVENTION

The invention relates to a composition of glycosaminoglycans for the treatment of chronic ulcers, specifically diabetic foot ulcers and pressure ulcers. It more particularly relates to compositions of low molecular weight heparins (LMWHs) and very low molecular weight heparins (VLMWHs) in the treatment of chronic ulcers, and more specifically in the manufacture of a medicinal product for the treatment of chronic ulcers.

STATE OF THE ART

Diabetes Mellitus (DM) is a metabolic disease which is characterized by a sustained increase of plasma glucose levels, which contributes to the onset of peripheral neuropathy and of macro- and microvascular complications. According to the data published by the World Health Organization (WHO), the incidence of DM is increasing in an alarming manner, a prevalence of 2.8% in the world population in 2000 and an increase of this figure to 4.4% in 2030 being estimated. Thus, the number of patients with DM was about 171 million in 2000 and it is estimated that this number will increase to 366 million in 2030. This increase in the incidence of DM has been associated, among other factors, with the general aging of the population, as there is a direct relationship between age and the prevalence of the disease. In this sense, it has been estimated that the prevalence of DM in Spain could be between 2% and 6%; 10% would correspond to DM type 1, 50% of the patients with DM type 2 being undiagnosed. Taking into account that the published studies of prevalence of DM in different regions of Spain are before 2002 and the tendency to the increase of the incidence, it is estimated that there are currently more than 2.5 million diabetic people in Spain.

The neurological damage, both of the peripheral and of the autonomic system probably represents the most common complication of DM. It can occur on both types of DM, and its prevalence and severity is related to the years of evolution of the diabetes and with the degree of glycemic control. It is estimated that this complication affects 60% of DM subjects, being the main cause of the onset of ulcers in the feet of diabetic subjects. In this line, the American Diabetes Association in its sixtieth scientific session established that 15% of the patients with DM developed throughout their life a foot ulcer and that foot ulcers are the cause of 6% of the hospitalizations occurring in diabetic subjects. 15% of all the ulcers occurring in patients with diabetes ends in amputation, the complications associated with DM being the main cause of non-traumatic amputations (40-70%), 85% of the amputations occurring in diabetic patients in turn being related to foot ulcers. In the United States, 100,000 amputations are performed yearly, which considerably affects healthcare costs, it being calculated that in 2001 ulcers and amputations had an approximate cost of 1000 million dollars in the US and this expense being 456 million dollars in UK. These costs derived from diabetic foot ulcer vary to a great extent depending on whether or not there has been amputation and thus, in a study conducted in Switzerland in 1990, it was observed that in the case of those ulcers which healed and had no ischemic component, the associated costs were 16,500 dollars. In contrast, in the cases in which a minor amputation was necessary, the costs reached 27,000 dollars, amounting to 63,000 dollars in the event that a major amputation occurred.

The definition of diabetic foot proposed by the Grupo de Consenso sobre Pie Diabético (Group of Consensus on Diabetic Foot) of the Spanish Society for Angiology and Vascular Surgery is: "Clinical alteration with a neuropathic etiopathogenic basis induced by maintained hyperglycemia in which, with or without the coexistence of ischemia, and after a traumatic trigger, foot lesion and/or ulceration occurs".

Foot ulceration is a significant complication of diseases such as diabetes with a yearly incidence slightly greater than 2% (Abbott C. A., et al. (2002) The North-West Diabetes Foot Care Study: incidence of, and risk factors for, new diabetic foot ulceration in a community-based patient cohort. Diabet. Med. 19(5):377-84). It is estimated that 15% of the patients with diabetes will develop ulcers at some time of their life (Reiber G. E. (1996) The epidemiology of diabetic foot problems. Diabet. Med. 13 Suppl 1:S6-11) and that about 10%-30% of those having ulcers will progress with the amputation of the limb (Lipsky B. A. (2004) Medical treatment of diabetic foot infections. Clin. Infect Dis. 39 Suppl 2:S104-14). Furthermore, this is complicated in the event that there is an ischemia in the lower limb in which the ulcer appears, occurring in most cases due to insufficient blood supply due to a high incidence of thrombosis.

In relation to the 5-year mortality of the patients who have undergone an amputation of lower limbs, it is 50-60% (Reiber G. E. (1996) The epidemiology of diabetic foot problems. Diabet. Med. 13 Suppl 1:S6-11). Various methods for the treatment of the patient with diabetic foot have been used which include strict metabolic control, prophylaxis of the modifiable risk factors, debridement, use of dressings, antimicrobial treatment of infections, elimination of the pressure of the lesioned area, use of skin grafts, administration of growth factors and use of revascularization methods in the event that there is indication.

In most cases, the treatment of this type of chronic ulcer is carried out by topical route, for example, the use of dressings in ulcers such as diabetic foot ulcers is common. The new types of dressings studied in controlled clinical trials include the dressings based on semipermeable polymeric membrane, Promogran (collagen matrix), alginate, carboxymethylcellulose, hyaluronan and subatmospheric pressure (Eldor R. et al. (2004) New and experimental approaches to treatment of diabetic foot ulcers: a comprehensive review of emerging treatment strategies. Diabet. Med. 21(11):1161-73). Methods for creating skin substitutes which are placed on the ulcerative lesion have also been developed. Dermagraft® is produced by seeding human dermal fibroblasts on a synthetic scaffold of bioabsorbable material which has proved to be effective in low-grade ulcers with a greater healing proportion in less time (Marston W. A., et al. (2003) Dermagraft Diabetic Foot Ulcer Study Group. The efficacy and safety of Dermagraft® in improving the healing of chronic diabetic foot ulcers: results of a prospective randomized trial. Diabetes Care 26:1701-5). Apligraf® consists of a dermal layer formed from human fibroblasts in a bovine type I collagen matrix and an epidermal later formed from human keratinocytes. Similarly, this skin substitute has proved to be significantly associated with a greater and faster healing of lesions when it is applied in low-grade and noninfected neuropathic ulcers (Veves A., et al (2001) Graftskin, a human skin equivalent, is effective in the management of noninfected neuropathic diabetic foot ulcers: a prospective randomized multicenter clinical trial. Diabetes Care 24:290-5). In a phase III, randomized, double-blind, placebo-controlled clinical trial, the Platelet Derived Growth Factor (PDGF) in the form of gel proved to be effective and safe for the treatment of diabetic patients having neuropathic ulcers with good blood perfusion (Wieman T J., et al. (1998) Clinical efficacy of beclapermin (rh PDGF-BB) gel. Diabetes Care 21 (5):822-7). Most of the patients (95%) included in this study had ulcers with an area <10 cm$^2$ according to the evaluation by planimetry. The 100 μg/g becaplermin gel, compared with placebo, significantly increased the complete lesion closure proportion by 43% (50 vs. 35%, p=0.007) and reduced the time to achieve said effect by 32% (86 vs. 127 days, p=0.013). The satisfactory results with PDGF or becaplermin (Regranex®) led to their approval for the treatment of neuropathic ulcers in the lower limbs of diabetic patients which extend to the subcutaneous tissue or deeper and have a suitable blood flow (Brem H., Sheehan P., Boulton A J. (2004) Protocol for treatment of diabetic foot ulcers. Am. J. Surg. 187(5A): 1 S-1 OS). However, a few months later the FDA commenced a safety review after receiving the data of a study which showed a greater risk of cancer in patients with diabetes who applied the topical growth factor Regranex© of Johnson & Johnson directly on the diabetic foot and leg ulcers, therefore this therapeutic alternative is currently under review and has been limited for patients who do not have a predisposition to suffering from any type of tumor.

In relation to treatments by local parenteral route, a method for administering a healing agent such as the Epidermal Growth Factor (EGF) was published a few years ago, which consists of the infiltration of a solution of the biomolecule into the lesion by means of several injections (WO 03053458). This treatment has proved to be effective in preventing the amputation of the diabetic foot but it has the drawback that it is traumatic for the patient since the application of injections into the lesion is very painful and several injections must be applied for several weeks in each treatment. Also, document EP 1499317 discloses a method for treating diabetic complications such as diabetic foot with sodium-hydrogen exchanger type 1 (NHE-1) inhibitors, and international publication WO 02077155 describes that the keratinocyte growth factor (KGF-2) promotes or accelerates the healing of lesions.

Finally, international publication WO2007087759 relates to a pharmaceutical composition containing microspheres with epidermal growth factors for parenteral administration for patients having chronic skin conditions, such as diabetic foot ulcers. Many other patents have focused on other methods for accelerating the healing range. However, none of these methods has proved to be widely effective.

In addition, several studies have been in published in non-patent literature which discloses certain promising results for diabetic foot patients treated with low molecular weight heparins (LMWHs), on the basis that heparins are known anti-thrombotic agents and anti-inflammatory agents which can improve vascular microcirculation. In "Effect of Dalteparin of healing of chronic foot ulcers in diabetic patients with peripheral arterial occlusive disease", Diabetes Care, vol. 26(9), September 2003, as well as in the publication of the same group of M. Kalani, A. et al., entitled "Beneficial effects of dalteparin on haemostatic function and local tissue oxygenation in patients with diabetes, severe vascular disease and foot ulcers", Thrombosis Research. 120, 653-661, 2007, clinical trials which demonstrate that a low molecular weight heparin (LMWH) such as dalteparin improves the evolution of diabetic foot ulcers in patients with peripheral arterial occlusive disease are described. However, it is striking that in these articles the patients are treated jointly with acetylsalicylic acid, i.e., it is suggested how the association of two active ingredients with anti-coagulating effect synergically favor the evolution of diabetic foot ulcers in patients with peripheral arterial occlusive disease. "Low molecular weight heparin seem to improve local capillary circulation and healing of chronic foot ulcers in diabetic patients", VASA, Brand 22, 1993, FET 2 also discloses double-blind, placebo-controlled clinical trials for evaluating the efficacy of dalteparin in patients with diabetic foot ulcers. The preliminary results of this study seem to indicate that dalteparin could have a beneficial effect on the prevention of this type of wound, although always in prophylactic doses, i.e., at no time are doses of dalteparin greater than 2500 IU/day used, since hemorrhages during the treatment at greater doses are foreseen, without this increase involving a greater efficacy in the case patients with diabetic foot ulcer. This is due to the general belief in the state of the art that diabetic patients have a greater bleeding risk than patients who do not have the disease (Adverse impact of bleeding on prognosis in patients with acute coronary syndromes, Eikelboom J W et al. Circulation. 2006 Aug. 22; 114(8):774-82).

BRIEF DESCRIPTION OF THE INVENTION

The use of glycosaminoglycans in the treatment of chronic ulcers, specifically diabetic foot ulcers, and particularly the use of some low molecular weight heparins for this purpose, has to date been roughly described for patients having severe circulatory conditions, since these low molecular weight heparins have antithrombotic and anti-coagulating activity, expressed as anti-activated factor X (Xa) effect and anti-factor IIa effect. However, they are generally not used for diabetic patients who suffer from diabetic foot ulcer without peripheral arterial occlusive disease, due to the bleeding risk involved in the treatment at greater doses. This is due to the anti-factor Xa effect of this type of compound, which translates into antithrombotic effect and which has a direct relationship with the content within the heparinoid structure of a specific pentasaccharide present in the saccharide structures forming low molecular weight and very low molecular weight heparins and to the anti-factor Xa/anti-factor IIa effect ratio. This ratio is determined because the larger the amount of pentasaccharide in the total structure, the greater the anti-factor Xa activity, the synthetic pentasaccharide (fondaparinux) being the most selective factor Xa inhibitor and therefore the molecule with the greatest antithrombotic capacity in a selective manner.

Therefore, the antithrombotic activity of fondaparinux is the consequence of the selective inhibition of factor Xa, mediated by antithrombin III (ATIII). Due to its selective binding to ATIII, the fondaparinux enhances 300 times the innate neutralization of factor Xa by ATIII. The neutralization of factor Xa interrupts the blood coagulation cascade and inhibits thrombin formation and thrombus development (see FIG. 1).

Taking into account the state of the art, it could initially be thought that a large amount of pentasaccharide in the structure will be necessary to obtain a curative (non-palliative) effect. However, as has been indicated above, this approach is not carried out due to the bleeding risk involved in the treatment at greater doses. The inventors of the present invention have achieved overcoming this prejudice of the state of the art since they have managed to demonstrate that, although the pentasaccharide is in a smaller proportion or chemically or enzymatically altered in a selective manner, the healing and regenerative effect is not affected, since what is really important in the structure of the glycosaminoglycan is the proportion of polysaccharide chains which do not contain the pentasaccharide. Furthermore, the investigators of the present invention have been able to experimentally determine the beneficial healing effect of the administration of the glycosaminoglycans with less amount of pentasaccharide in any type of ulcer which is considered to be chronic—not only in diabetic foot ulcers—and that said administration is effective by means of three main routes of administration: parenteral, oral and topical route.

It was due to the works conducted at the start of the 1980s by the groups of Lindahl and Choay (Choay J, Lormeau J C, Petitou M, Sinag P and Fareed J. Ann NY Acad Sci 1981; 370:644-649; Thunberg L, Bäckström G and Lindahl U. Carbohydr Res 1982; 100:393-410) that the hypothesis that within heparin chains there is a specific sequence corresponding to a pentasaccharide which interacts selectively with antithrombin III was made. The structure of this pentasaccharide is the following (formula 1):

pentasaccharide with affinity for antithrombin III are equally important, it is thus possible to establish how the elimination of any of these groups affects the anti-Factor Xa activity of the latter:

For this reason, in the present invention different LMWHs or VLMWHs (see examples) have been physically and chemically modified to alter the pentasaccharide responsible for the anti-FXa activity in a qualitative and quantitative manner, to demonstrate that in the case of ulcers, specifically diabetic foot ulcers, what is of interest is that in this type of glycosaminoglycans there is a greater proportion of oligosaccharide sequences rich in the monosaccharides selected from the group consisting of: N-sulfo-D-glucosamine and D-glucuronic acid, and in preferred embodiments of the invention, also N-acetyl-D-glucosamine, L-iduronic acid and 2-sulfated L-iduronic acid and not as much of the pentasaccharide responsible for the anti-FXa activity (the presence of high concentrations of the N-sulfo-3O-sulfo-D-glucosamine unit essential for the antithrombotic activity of the pentasaccharide not being necessary). For this reason, for the purposes of the present invention the proportion of pentasaccharide is limited to a maximum of 20% of the characteristic disaccharide of the pentasaccharide (D-glucuronic acid bound to N-sulfo-3-sulfo-D-glucosamine) in the structure of the glycosaminoglycan which, according to the state of the art, is Formula 1

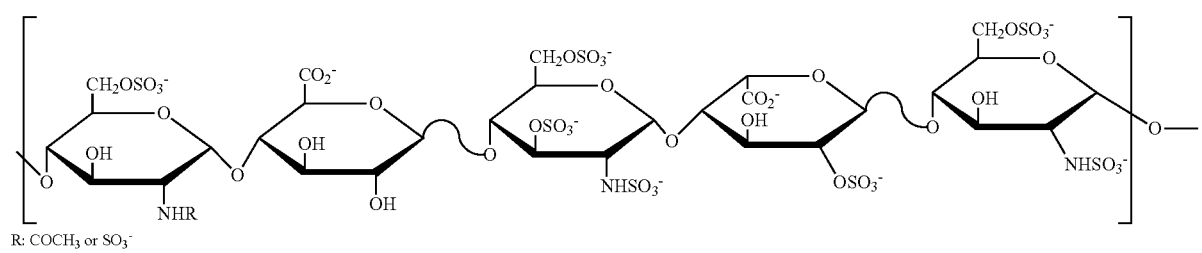

R: COCH$_3$ or SO$_3^-$

In non-fractionated heparin as well as in the various LMWHs or VLMWHs obtained by known depolymerization methods (enzymatic, nitrous acid, β-elimination, etc), there is a measurement which allows determining the amount of pentasaccharide within the general structure through the quantification of the content of a specific and exclusive disaccharide unit of the pentasaccharide called D-glucuronic acid bound to N-sulfo-3-sulfo-D-glucosamine ($A_{NS,3S}$). This measurement allows obtaining a good correlation between the percentage present of this disaccharide and the content of pentasaccharide in the heparin structure and therefore of anti-FXa activity of the heparin in question (Guerrini M et al. Seminars in Thrombosis and Hemostasis 2007; 33: 478-787).

The different chemical and/or enzymatic modifications which can affect the integrity of the pentasaccharide would also have correlated thereto a decrease of the anti-FXa activity of the compound. These reactions can be de-N-acetylations, N and O-sulfations, O-acylations, ring opening reactions, etc.

For example, if the pentasaccharide is chemically or enzymatically altered in relation to the degree of sulfation, the anti-Factor Xa effect is also altered. However, in various studies (Lindahl U, Bäckström G and Thunberg L. J. Biol. Chem. 1983; 258:9826-9830; Riesenfeld J, Thunberg L, Höök M and Lindahl U. J. Biol. Chem. 1981; 256:2389-2393), it has been demonstrated that when the degree of sulfation is altered not all the sulfate groups present in the responsible for the anti-FXa activity and which therefore, according to the latter, would be suitable to have a greater proportion.

The state of the art clearly shows that diabetic patients have the healing process of ulcers caused by the disease itself altered, but the inventors of the present invention gave also demonstrated that the effect of the pharmaceutical composition object of the present invention surprisingly works for all types of ulcers, both chronic and pressure ulcers.

For the object of the present invention, chronic ulcers are understood as the solutions of continuity with loss of substance in the skin, depending on the origin of the ulcer they can be classified as: pressure ulcers, diabetic ulcer, ischemic (arterial or venous) ulcer, post-burn ulcer, post-radiotherapy ulcers, etc.

This classification has been made according to the cause generating ulcer, however the physiopathological mechanism converting a wound/ulcer into chronic is an alteration in the ischemic process leading to cutaneous necrosis and to a regenerative difficulty thereof by natural means (Kirman C N. Pressure ulcers, non surgical treatment and principles, Emedicine July 2008 (www.emedicine.com/plastic) An G, Faeder J, Vodovotz Y. Transactional systems biology: introduction of an engineering approach to the pathophysiology of the burn patient. J Burn Care Res. 2008; 29(2):277-85. Nikolovska S, et al. The role of nitric oxide in the pathogenesis of venous ulcers. Acta Dermatovenerol Croat 2005; 13(4):242-6).

In this sense, for example ischemia can occur due to external pressure on the capillaries (decubitus or pressure ulcers), due to injury by heat (burn), or due to vascular obstruction (diabetes, arteriosclerosis, etc.). After the ischemic process of the skin and surrounding organs, there is a reperfusion of the damaged tissues, which increases the initial lesion leading to a worsening and aggravation of the lesions. The exact mechanism of the ischemia-reperfusion process aggravating the initial lesion and leading to the chronicity of the lesion, occurring after the initial necrosis, is not known but it is suspected that the continuous production of inflammatory mediators (cytokines, interleukin, etc.) aggravates the initial ischemic process, worsening the lesions, and leading to the chronicity of the ulcer.

To that end, different therapeutic weapons for modeling the production of inflammatory mediators which facilitate tissue regeneration, but do not worsen cell damage, have been investigated. A fact to be emphasized is that the healing process of a wound is the same in almost all tissues, after the exposure to any destructive process (Gurtner G C et al. Wound repair and regeneration. Nature 2008; 453:314-21); research has thus been recently conducted with low molecular weight heparins in the prevention of the burn wounds (Ravikumar T et al. Low molecular weight heparin-induced pharmacological modulation of burn wound healing. Ann Burn fire Disast 2006; 19(3): 1-10 Oremus M, et al. The uses of heparin to treat burn injury. Evid Rep Technol Assess (Full Rep). 2006; (148):1-58) but to date there is no systemic treatment facilitating the regeneration of a chronic ulcer (Fonder M A et al. Treating the chronic wound: A practical approach to the care of nonhealing wounds and wound care dressings. J Am Acad dermatol 2008; 58:185-206) and even less is it known in the case of glycosaminoglycans which is the composition and/or percentage of monosaccharides responsible for this healing and regenerative activity favoring the appearance of physiological systems such as the blocking of the production of inflammatory mediators, capillary regeneration, or ulcer reperfusion and healing mechanisms.

In other words, the composition object of the present invention works for chronic ulcers even for patients who do not have diabetes and in whom there is an onset of a certain type of chronic ulcer which does not heal easily, such as pressure ulcers, understanding pressure ulcers as those having areas of damage in the skin and underlying tissue caused by the prolonged pressure on a hard plane, not necessarily intense, and independent of the position. The term decubitus ulcer is currently discarded because it does refer to the pressure, a determining factor in its onset, and because it excludes those which have not appeared in decubitus position.

It is a common problem in the care of patients with chronic diseases, especially in elderly patients with limited mobility, with considerable morbi-mortality and high economic and social repercussion, therefore for the object of the present invention it is important to determine that although most of the examples have been carried out causing diabetes in the animals, in Example 5 it is clearly seen how the administration of the pharmaceutical composition object of the present invention works surprisingly well although the animal is not diabetic.

Furthermore, without wishing to be bound by theory, the inventors believe, however, that this hypothesis is supported by the results of their examples, because if the synthetic pentasaccharide (fondaparinux) is used for the treatment of ulcers, and specifically of diabetic foot ulcers, the healing and/or regenerative activity is highly reduced (when it should be the reverse) in the same manner as if the monosaccharides selected from the group consisting of N-sulfo-D-glucosamine and D-glucuronic acid, as well as, in preferred embodiments of the invention, also N-acetyl-D-glucosamine, L-iduronic acid and 2-sulfated L-iduronic acid, are chemically and/or enzymatically modified, the activity of the glycosaminoglycan of the inventors decreases drastically. It is therefore concluded that although there is a pentasaccharide portion in the structure, it is not responsible for the tissue healing and/or regenerative activity, as well as if the aforementioned monosaccharides are qualitatively or quantitatively altered, a good tissue healing and/or regenerative activity is not obtained.

For this reason, a main aspect of the present invention is aimed at a composition of glycosaminoglycans containing a proportion of certain monosaccharides and containing a proportion which does not exceed 20% of the characteristic disaccharide of the pentasaccharide, for the treatment of chronic ulcers and particularly of diabetic foot ulcer.

The inventors of the present invention have also prepared a relationship between the necessary amount of the aforementioned monosaccharides and the dose of a medicinal product containing a pharmaceutically effective amount of glycosaminoglycan, relating the proportion of monosaccharides (IU) with the plasma half-life of the product, to achieve a disease "treatment" dose and not a prophylaxis dose.

In the studies published to date, the objective of the few heparins used for chronic ulcers, and specifically diabetic foot ulcers, has always been prophylaxis, i.e., it was believed that the increase of the dose would cause a hemorrhage in the patient, or a coadjuvant therapy of the disease with another type of compound acting at different levels in the coagulation cascade, such as ASA. Therefore, the conditions used in these cases have been the usual ones for prophylaxis, which involves using very low concentrations of heparin, the ratio between the plasma half-life (in hours) and the dose in IU being 1:472 for the case of bemiparin, for example.

This is so because the effect sought with heparin is acting in prophylaxis since, taking into account the state of the art, the amount of pentasaccharide responsible for the antithrombotic activity is more than enough to favor lower limb vascularization in patients with diabetic foot ulcer, and at doses greater than the indicated dose the general belief is that the bleeding risk increases due to the excess of said antithrombotic effect, taking into account that diabetic patients have a greater predisposition to bleeding, without realizing that what is really important is administering a larger amount of other monosaccharides which do not form part of the pentasaccharide in the formulation. Therefore, very low doses have traditionally always been used for this purpose, in which the ratio between the plasma half-life and the dose in IU of the LMWH is less than 1:500, since it is considered that the same anti-coagulating and antithrombotic effect but with a lower bleeding risk for patients who already have a complex disease such as diabetes is thus achieved.

To the inventors' knowledge, there is substantially no patent literature on the treatment of diabetic foot ulcers with compositions of glycosaminoglycans such as low molecular weight heparins without them being prophylaxis doses, since the latter are not curative but rather preventive and do not actually cure ulcers by means of healing with granulation tissue regeneration, but rather they are used because it is believed that they prevent the formation thereof and in most cases are used in synergic treatment with other drugs such as acetylsalicylic acid (Effect of Dalteparin of healing of chronic foot ulcers in diabetic patients with peripheral arterial occlusive disease", Diabetes Care, vol. 26(9), September 2003; M. Kalani, A. et al. entitled Beneficial effects of dalteparin on haemostatic function and local tissue oxygenation in patients with diabetes, severe vascular disease and foot ulcers. Thrombosis Research. 120, 653-661, 2007).

Furthermore, the inventors of the present invention have achieved eliminating the prejudices of the state of the art, since they have determined that in the case of certain glycosaminoglycans, such as LMWHs and VLMWHs, the amount of pentasaccharide for the treatment of diabetic foot ulcers (in diabetic patients) is not significant, but rather what is really important is the presence of a proportion of oligosaccharide sequences rich in certain specific monosaccharides. This proportion of certain specific monosaccharides, mentioned in the detailed description of the present invention, is responsible for the healing of this type of ulcer in diabetic patients, since when this type of glycosaminoglycan is administered by subcutaneous route or by parenteral route, the healing effect is due to the presence of certain oligosaccharide fractions which do not contain the pentasaccharide commonly linked in the state of the art to the anti-factor Xa effect in low molecular weight and very low molecular weight heparins. Furthermore, the inventors of the present invention have determined that provided that the pentasaccharide is slightly (quantitatively and qualitatively) altered in the heparinoid structure, the anti-FXa activity decreases considerably. However, a similar decrease in the healing power is not observed.

Therefore, an important problem in the treatment of diabetic foot ulcers is achieving the effective and efficacious dose of a medicinal product, which achieves ischemic tissue regeneration and prevents the amputation of the diabetic foot and which is furthermore effective not only in prophylaxis but also as therapeutic treatment. Another additional advantage which the treatment of choice must have is that it is not very traumatic for the patient since diabetic foot ulcers are characterized by being extremely painful, therefore the route of administration must not be very traumatic in the proximity of the wound. Therefore, for the purposes of the present invention the preferred routes of administration are the parenteral route, the oral route and the topical route which is non-invasive or is directly applied on the mucosa to be treated.

The following signals have also been labeled:
ANSred, N-sulfo-D-glucosamine of the reducing end; ANS,3S, N-sulfo-3O-sulfo-D-glucosamine.

Figure 2A:
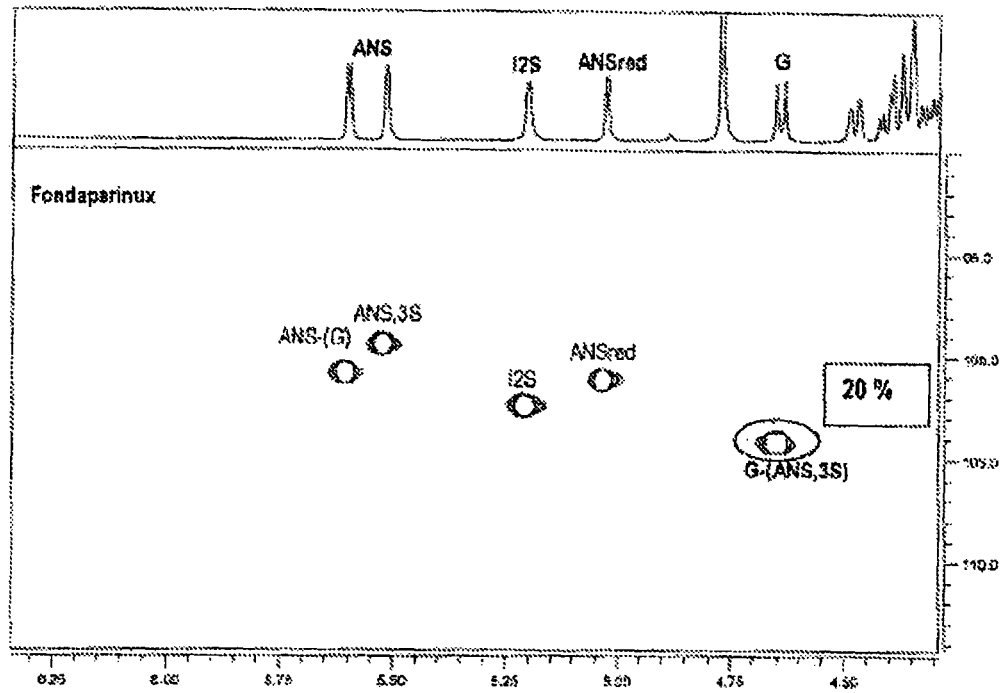
FIG. 2A depicts the region of the anomeric signals (H1-C1 correlations) of the $^{13}C$-$^{1}H$ HSQC spectrum of fondaparinux (pentasaccharide responsible for the interaction with antithrombin III) recorded at 298K in deuterated water ($D_2O$). In the spectrum, five correlation peaks corresponding to the five monosaccharides forming the pentasaccharide can be observed. ANSred, N-sulfo-D-glucosamine of the reducing end; I2S, 2-sulfated L-iduronic acid; ANS,3S, N-sulfo-3O-sulfo-D-glucosamine; G-(ANS,3S), D-glucuronic acid preceding the ANS,3S unit and ANS-(G), N-sulfo-D-glucosamine preceding the D-glucuronic acid ring. The H1-C1 correlation peak of the G-(ANS,3S) unit has been highlighted with a circle because it is the most characteristic signal of the pentasaccharide and will be taken as a reference to quantify the presence thereof in various samples. The proportion of this monosaccharide in fondaparinux is 20%.
Figure 2B:
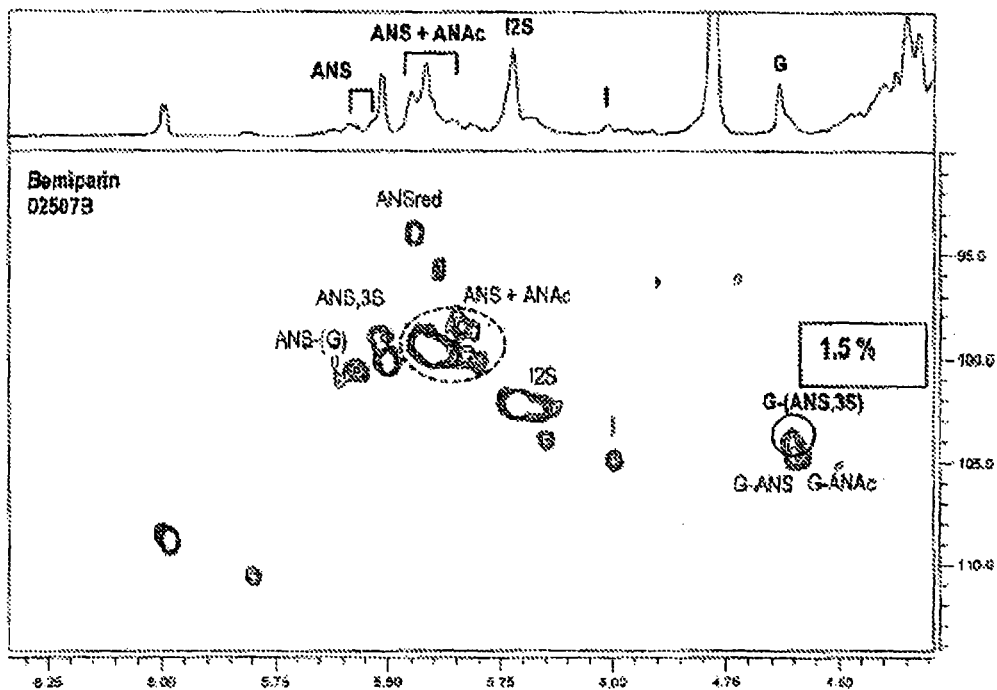
FIG. 2B depicts the region of the anomeric signals (H1-C1 correlations) of the $^{13}C$-$^{1}H$ HSQC spectrum of the low molecular weight heparin bemiparin, recorded at 298K in deuterated water ($D_2O$). The spectrum is much more complex than that obtained for fondaparinux (see FIG. 2A), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to the increase of the proportion of D-glucuronic acid bound to N-sulfo-D-glucosamine G-(ANS), the latter being the major glucuronic ring. The decrease of the proportion of the G-(ANS,3S) in the bemiparin samples, 1.5% of the total monosaccharide content, shows that most of the oligosaccharide chains do not have the structural motif responsible for the interaction with antithrombin III.
Figure 2C:
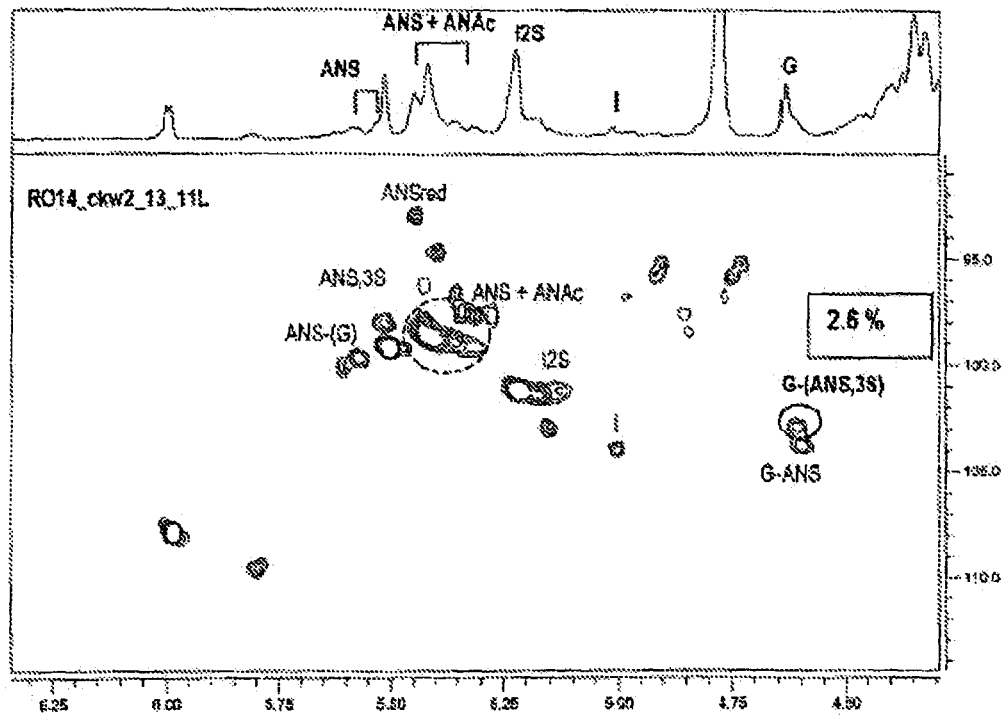

FIG. 2C depicts the region of the anomeric signals (H1-C1 correlations) of the $^{13}C$-$^{1}H$ HSQC spectrum of the very low molecular weight heparin RO14 ckw2__13__11L, recorded at 298K in deuterated water ($D_2O$). The spectrum is much more complex than that obtained for fondaparinux (see FIG. 2A), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to the increase of the proportion of D-glucuronic acid bound to N-sulfo-D-glucosamine G-(ANS), the latter being the major glucuronic ring. The decrease of the proportion of the G-(ANS,3S) unit in the RO14 ckw2__13__11L samples, 2.6% of the total monosaccharide content, shows that most of the oligosaccharide chains do not have the structural motif responsible for the interaction with antithrombin III.

The following signals have also been labeled:
ANSred, N-sulfo-D-glucosamine of the reducing end; ANS,3S, N-sulfo-3O-sulfo-D-glucosamine.

Figure 2D:
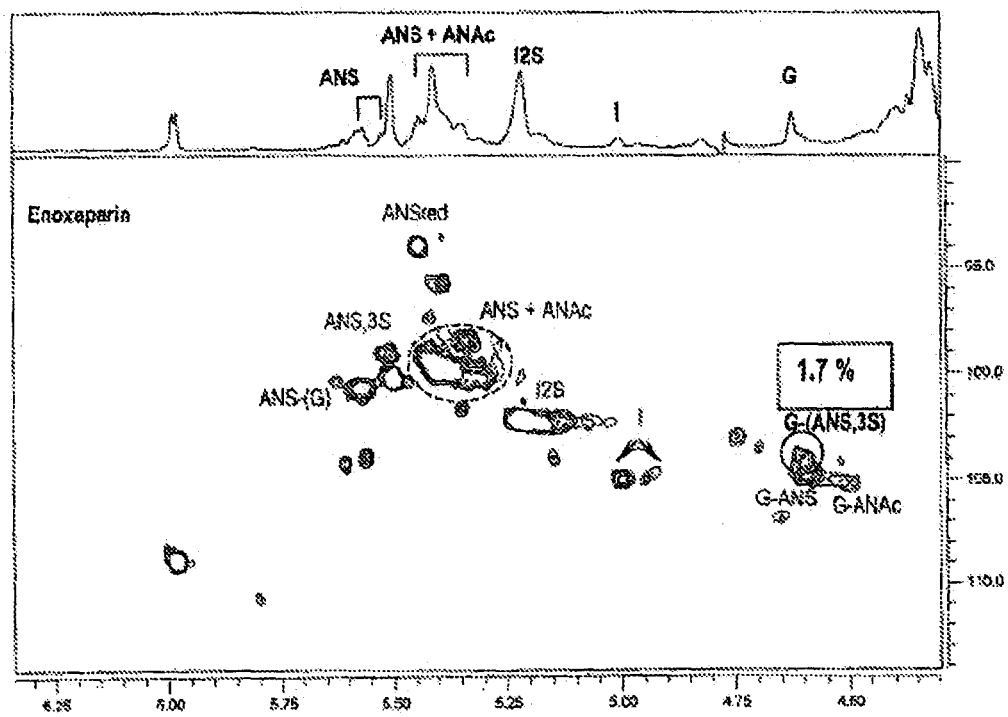

FIG. 2D depicts the region of the anomeric signals (H1-C1 correlations) of the $^{13}C$-$^{1}H$ HSQC spectrum of the low molecular weight heparin enoxaparin, recorded at 298K in deuterated water ($D_2O$). The spectrum is much more complex than that obtained for fondaparinux (see FIG. 2A), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to the increase of the proportion of D-glucuronic acid bound to N-sulfo-D-glucosamine G-(ANS), the latter being the major glucuronic ring. The decrease of the proportion of the G(ANS,3S) unit in the enoxaparin samples, 1.7% of the total monosaccharide content, shows that most of the oligosaccharide chains do not have the structural motif responsible for the interaction with antithrombin III.

The following signals have also been labeled:
ANSred, N-sulfo-D-glucosamine of the reducing end; ANS,3S, N-sulfo-3O-sulfo-D-glucosamine.

Figure 2E:
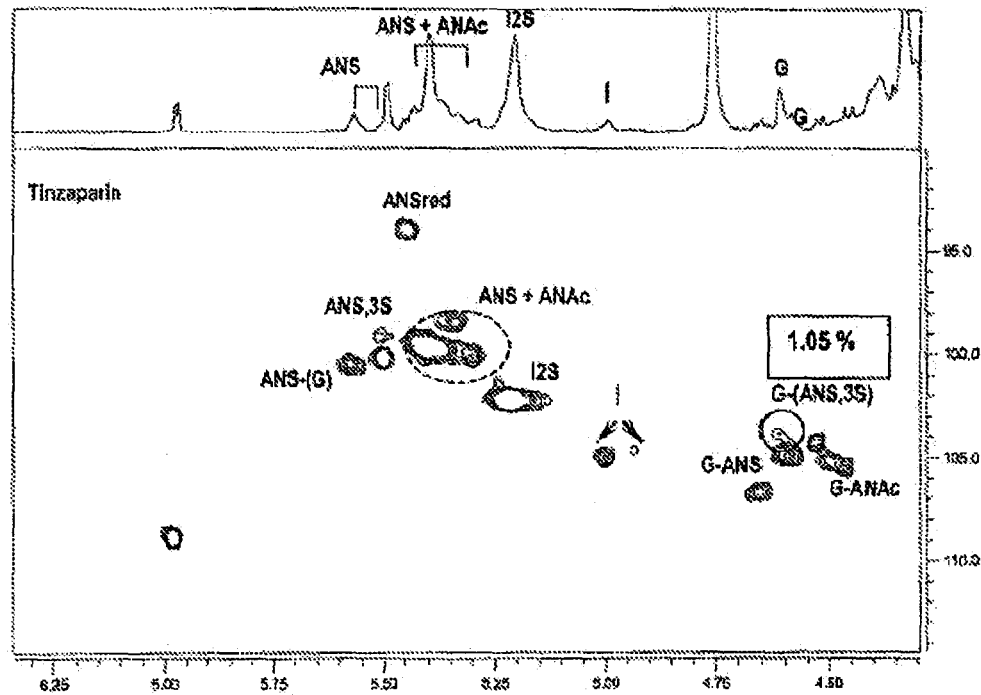

FIG. 2E depicts the region of the anomeric signals (H1-C1 correlations) of the $^{13}C$-$^{1}H$ HSQC spectrum of the low molecular weight heparin tinzaparin, recorded at 298K in deuterated water ($D_2O$). The spectrum is much more complex than that obtained for fondaparinux (see FIG. 2A), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to increase of the proportion of D-glucuronic acid bound to N-sulfo-D-glucosamine G-(ANS), the latter being the major glucuronic ring. The decrease of the proportion of the G(ANS,3S) unit in the tinzaparin samples, 1.05% of the total monosaccharide content, shows that most of the oligosaccharide chains do not have the structural motif responsible for the interaction with antithrombin III.

The following signals have also been labeled:

ANSred, N-sulfo-D-glucosamine of the reducing end; ANS,3S, N-sulfo-3O-sulfo-D-glucosamine.

Figure 2F:
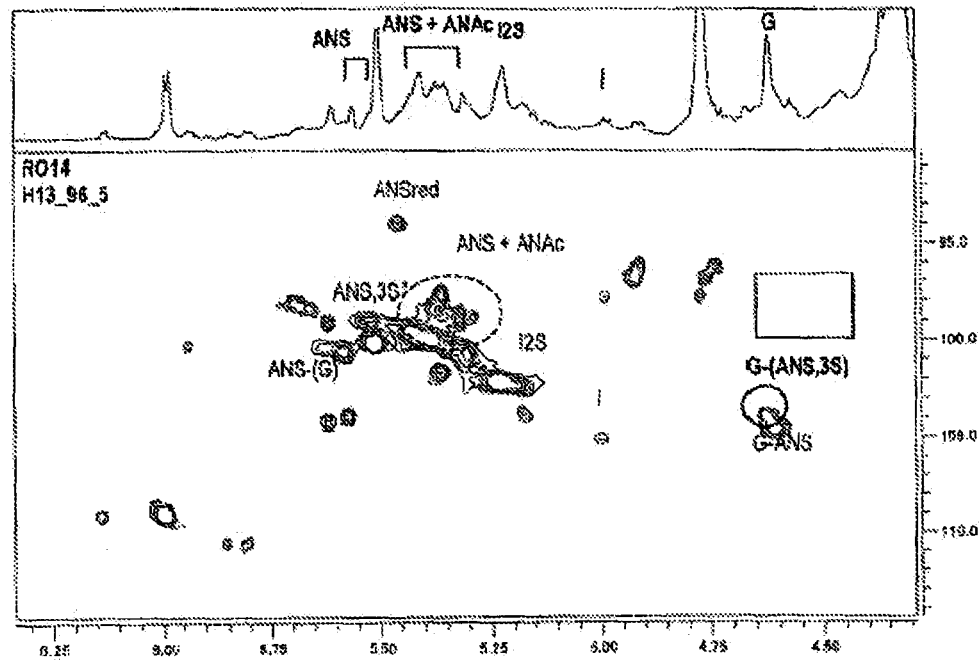

FIG. 2F depicts the region of the anomeric signals (H1-C1 correlations) of the $^{13}C$-$^{1}H$ HSQC spectrum of the very low molecular weight heparin RO14-H13-96-5, recorded at 298K in deuterated water ($D_2O$). The spectrum is much more complex than that obtained for fondaparinux (see FIG. 2A), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to the increase of the proportion of D-glucuronic acid bound to N-sulfo-D-glucosamine G-(ANS), the latter being the major glucuronic ring. The decrease of the proportion of the G-(ANS,3S) unit in the RO14_H13_96_5 samples, 1.9% of the total monosaccharide content, shows that most of the oligosaccharide chains do not have the structural motif responsible for the interaction with antithrombin III.

The following signals have also been labeled:

ANSred, N-sulfo-D-glucosamine of the reducing end; ANS,3S, N-sulfo-3O-sulfo-D-glucosamine.

FIG. 2G depicts the region of the anomeric signals (H1-C1 correlations) of the $^{13}C$-$^{1}H$ HSQC spectrum of the low molecular weight heparin BEMI_99_4, recorded at 298K in deuterated water ($D_2O$). The spectrum is very different from that obtained for fondaparinux (see FIG. 2A), due to the presence of new monosaccharide units which were not present in fondaparinux (I, non-sulfated L-iduronic acid; ANAc, N-acetyl-D-glucosamine) and to the disappearance of some of the characteristic signals such as ANS,3S and G-(ANS,3S). The disappearance of the signal of the pentasaccharide, G-(ANS,3S), shows that this type of low molecular weight heparin does not have detectable amounts of the structural motif responsible for the interaction with antithrombin III. Likewise, the disappearance of the signal of I2S shows that this LMWH also has significant changes in the characteristic units of the regular region of heparin.

Figure 1:
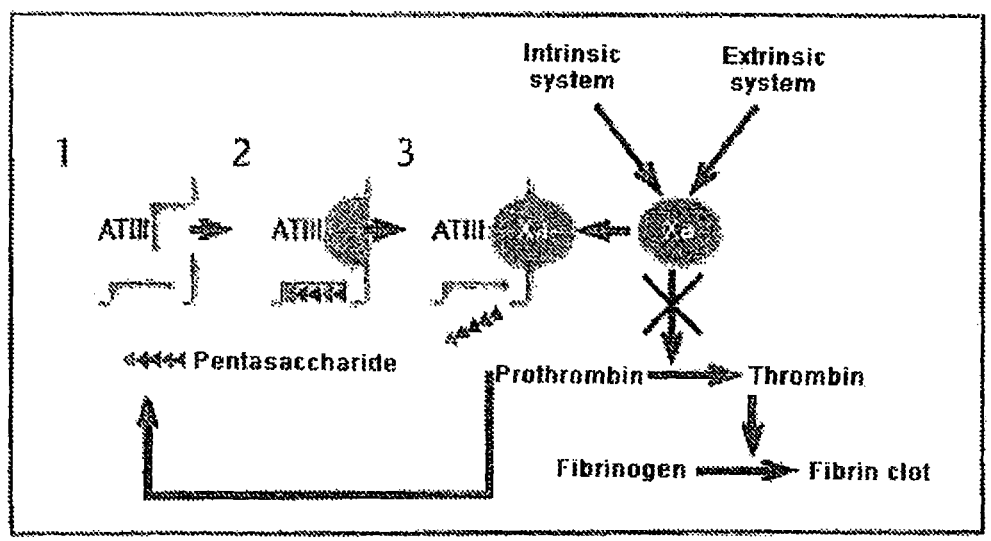
FIG. 1 depicts the mechanism of action of the synthetic pentasaccharide (fondaparinux).

FIG. 2H depicts the region of the anomeric signals (H1-C1 correlations) of the $^{13}C$-$^{1}H$ HSQC spectrum of heparin sodium, recorded at 298K in deuterated water ($D_2O$). The spectrum is much more complex than that obtained for fondaparinux (see FIG. 1), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to the increase of the proportion of D-glucuronic acid bound to N-sulfo-D-glucosamine G-(ANS), the latter being the major glucuronic ring. The decrease of the proportion of the G-(ANS,3S) unit in the heparin sodium samples, 1.0% of the total monosaccharide content, shows that most of the oligosaccharide chains do not have the structural motif responsible for the interaction with antithrombin III.

The following signals have also been labeled:

ANSred, N-sulfo-D-glucosamine of the reducing end; ANS,3S, N-sulfo-3O-sulfo-D-glucosamine.

Figure 2I:
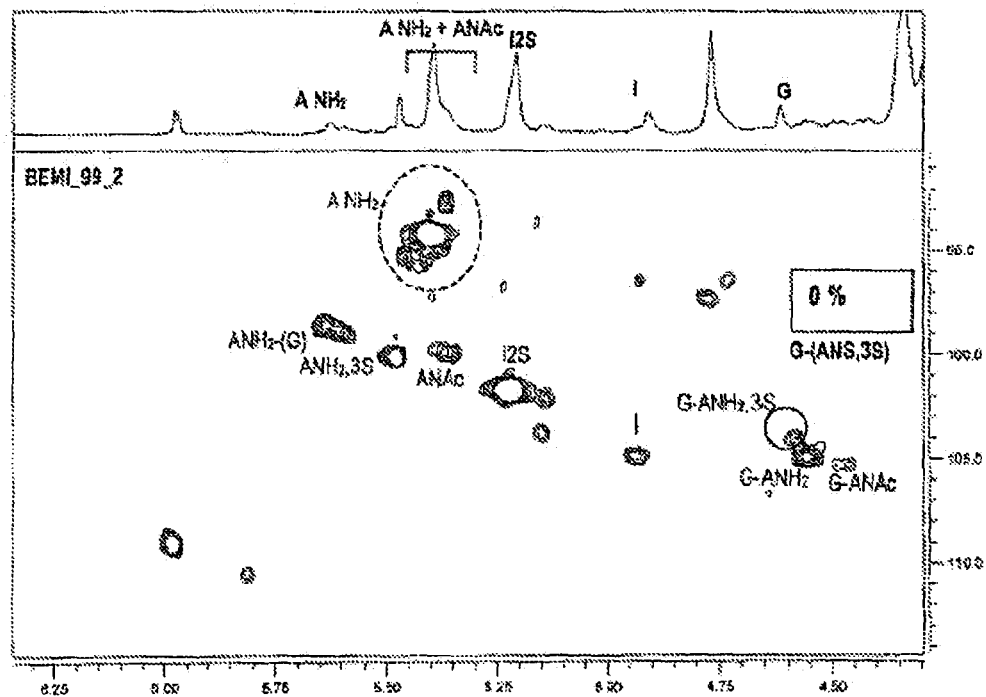

FIG. 2I depicts the region of the anomeric signals (H1-C1 correlations) of the $^{13}C$-$^{1}H$ HSQC spectrum of the low molecular weight heparin BEMI_99_2, recorded at 298K in deuterated water ($D_2O$). The spectrum is very different from that obtained for fondaparinux (see FIG. 1), due to the presence of new monosaccharide units which were not present in fondaparinux (I, non-sulfated L-iduronic acid; ANAc, N-acetyl-D-glucosamine; ANH2, D-glucosamine; ANH2, 3S, D-3-O-sulfo-glucosamine) and to the disappearance of some of the characteristic signals such as ANS,3S and G-(ANS,3S).

Figure 2J:
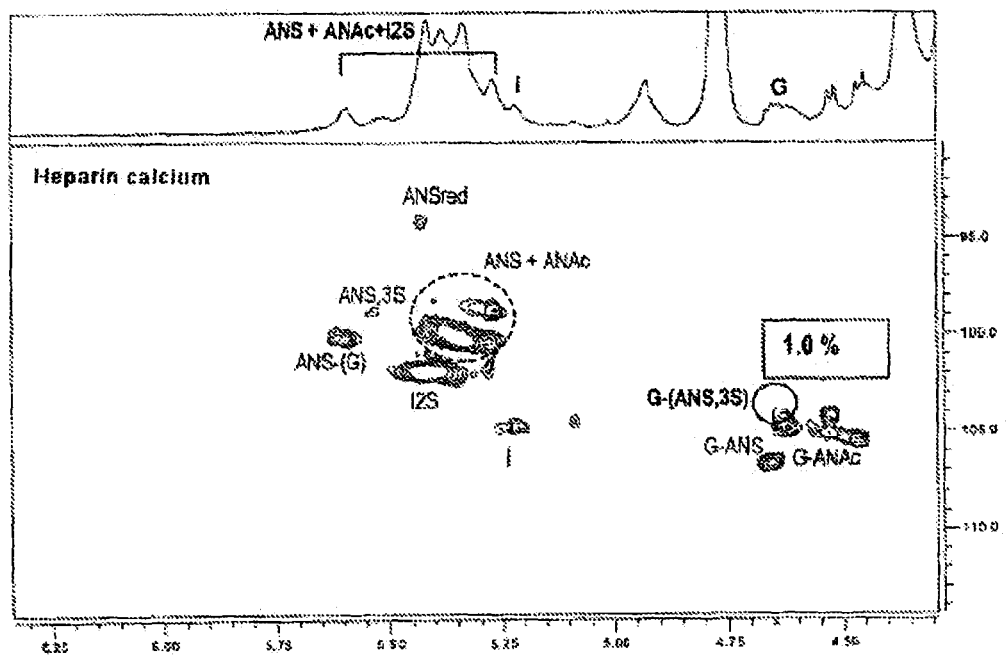

FIG. 2J depicts the region of the anomeric signals (H1-C1 correlations) of the $^{13}C$-$^{1}H$ HSQC spectrum of heparin calcium, recorded at 298K in deuterated water ($D_2O$). The spectrum is much more complex than that obtained for fondaparinux (see FIG. 1), due to the presence of new monosaccharide units which were not present in fondaparinux (I, non-sulfated L-iduronic acid; ANAc, N-acetyl-D-glucosamine) and to the alteration of the proportion of the existing units, as is the case of the 2-sulfated L-iduronic acid ring, I2S, which is present in a greater proportion. The H1-C1 correlation peak of the characteristic G-(ANS,3S) unit of the pentasaccharide has been highlighted with a circle. As can be observed in the figure, the intensity of this signal has decreased in comparison with the fondaparinux sample due to the increase of the proportion of D-glucuronic acid bound to N-sulfo-D-glucosamine G-(ANS), the latter being the major glucuronic ring. The decrease of the proportion of the G-(ANS,3S) unit in the heparin sodium samples, 1.0% of the total monosaccharide content, shows that most of the oligosaccharide chains do not have the structural motif responsible for the interaction with antithrombin III.

The following signals have also been labeled:

ANSred, N-sulfo-D-glucosamine of the reducing end; ANS,3S, N-sulfo-30-sulfo-D-glucosamine.

Figure 2K:
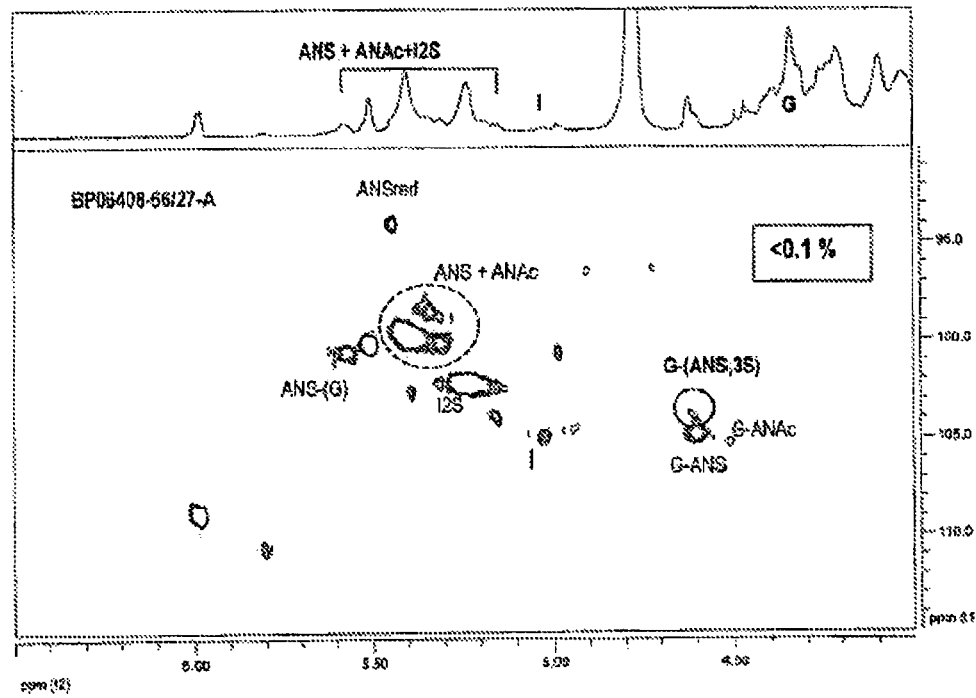

FIG. 2K depicts the region of the anomeric signals (H1-C1 correlations) of the $^{13}C$-$^{1}H$ HSQC spectrum of the low molecular weight heparin BP06408-66/27-A, recorded at 298K in deuterated water ($D_2O$). The spectrum is very different from that obtained for fondaparinux (see FIG. 2A), due to the presence of new monosaccharide units which were not present in fondaparinux (I, non-sulfated L-iduronic acid; ANAc, N-acetyl-D-glucosamine) and to the decrease of the signals corresponding to ANS,3S and G-(ANS,3S). The decrease of the signal of the pentasaccharide, G-(ANS,3S), shows that this type of low molecular weight heparin has a low concentration of the structural motif responsible for the interaction with the antithrombin III.

Figure 2L:
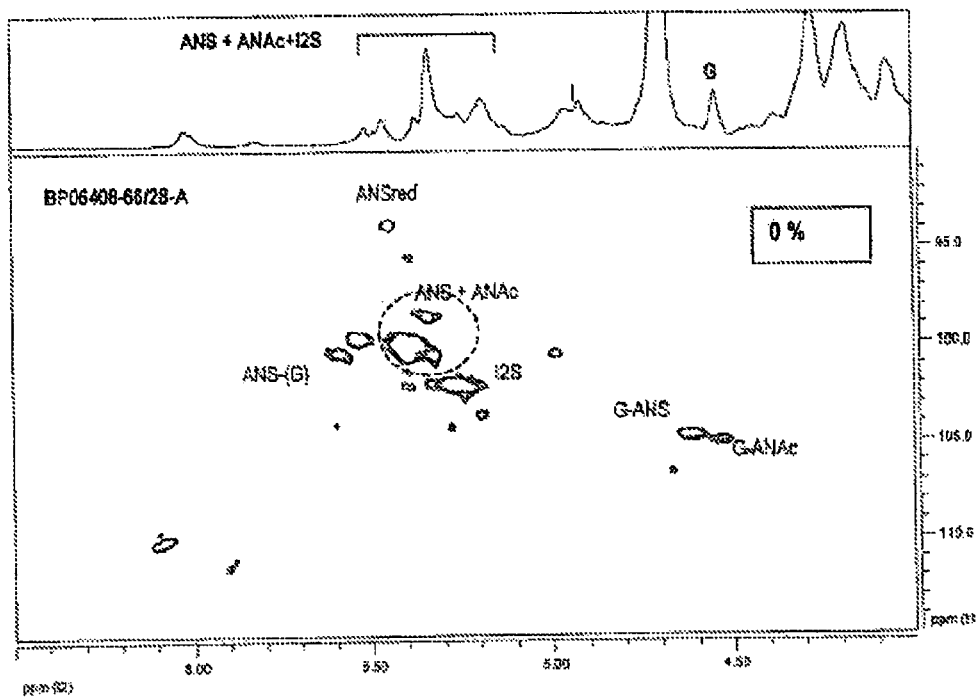

FIG. 2L depicts the region of the anomeric signals (H1-C1 correlations) of the $^{13}$C-$^{1}$H HSQC spectrum of the low molecular weight heparin BP06408-66/28-A, recorded at 298K in deuterated water (D$_2$O). The spectrum is very different from that obtained for fondaparinux (see FIG. 2A), due to the presence of new monosaccharide units which were not present in fondaparinux (I, non-sulfated L-iduronic acid; ANAc, N-acetyl-D-glucosamine) and the disappearance of the signals corresponding to ANS,3S and G-(ANS,3S). The disappearance of the signal of the pentasaccharide, G(ANS, 3S), shows that this type of low molecular weight heparin does not have detectable amounts of the structural motif responsible for the interaction with antithrombin III.

Figure 3:
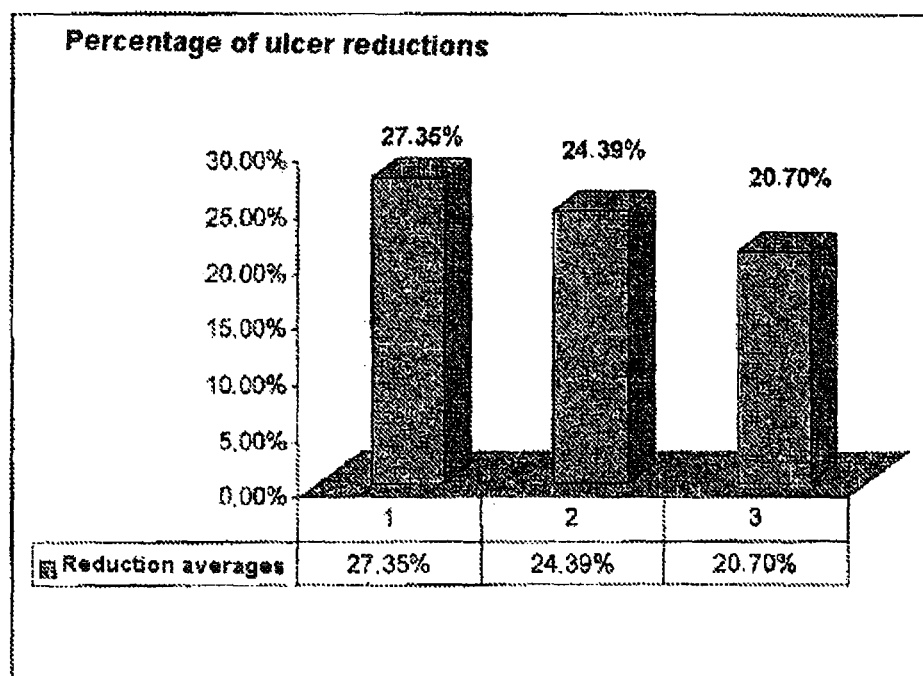

FIG. 3 shows the percentage of ulcerated area reduction in the mice of Example 2 when bemiparin is administered with a ratio between the half-life and the dose of 1:950, when bemiparin is administered with a ratio between the half-life and the dose of 1:472 and when fondaparinux is administered at equivalent treatment doses, i.e., 5 mg/ml, since it has a plasma half-life of 17 hours in healthy individuals, therefore in wistar rats it is 0.22 mg per rat.

Figure 4:
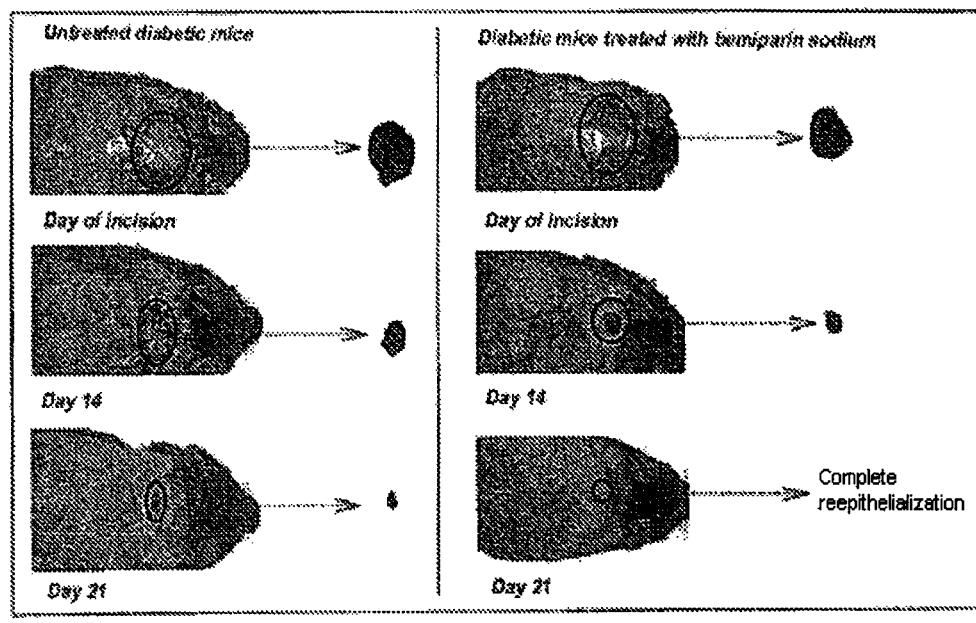

FIG. 4 shows the evolution of the diabetic control mice of Example 4 with respect to the mice treated with bemiparin sodium. The wound area has been depicted to the right of each animal.

Figure 5:
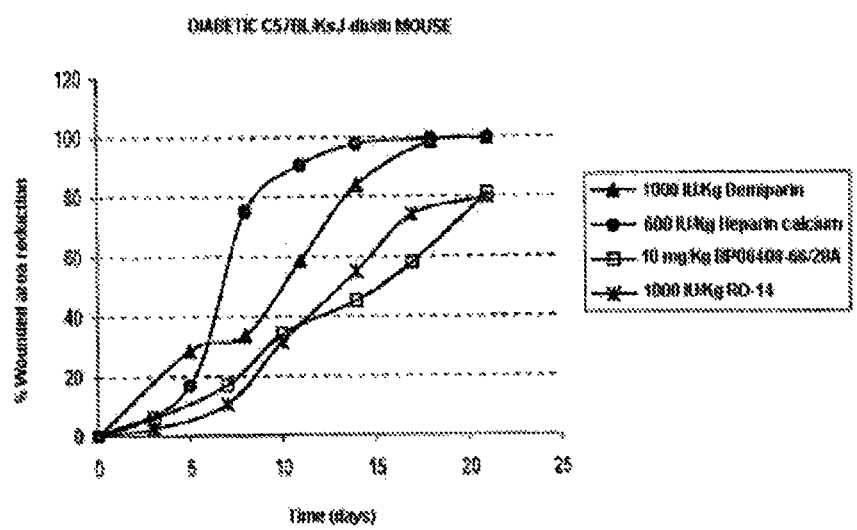

FIG. 5 shows the evolution of the percentage of healing of the wound over time in the mice of Example 4.

Figure 6:
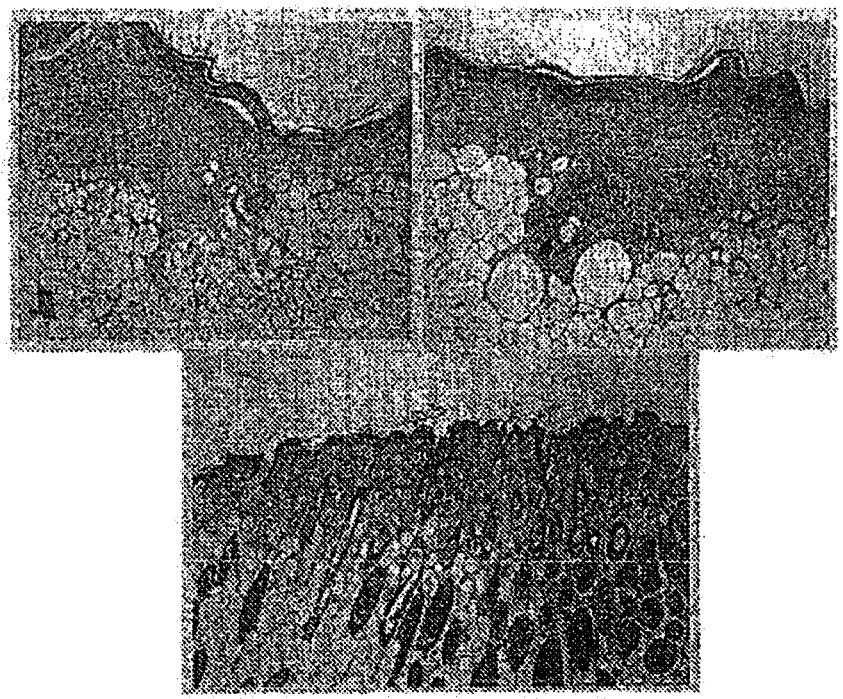

FIG. 6 shows microphotographs of the wound sections of the mice of Example 4 after the staining with hematoxylin-eosin. A diabetic control. B diabetic animal treated with fondaparinux sodium, C diabetic animal treated with bemiparin sodium.

Figure 7:
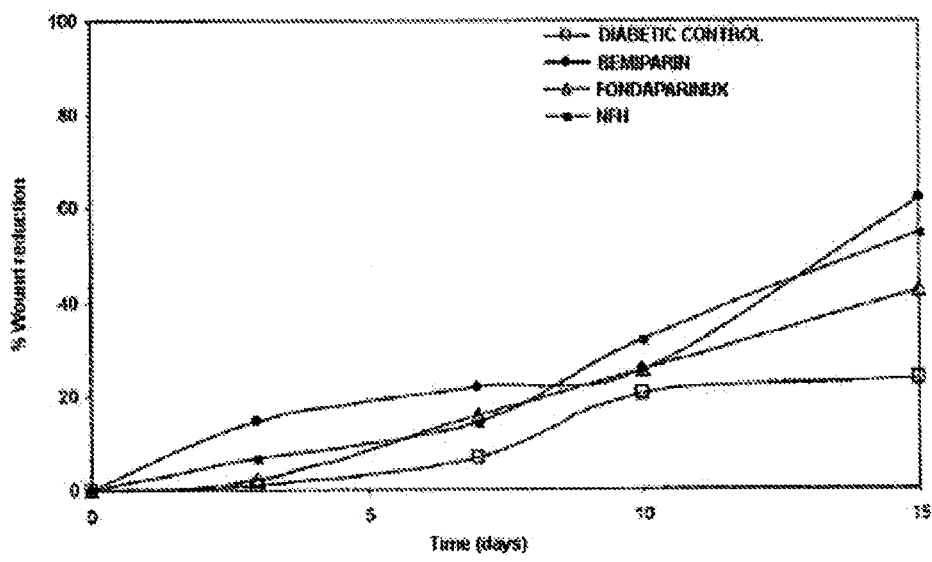

FIG. 7 depicts the percentage of ulcerated area reduction of the mice of Example 5 when a control composition by topical route, a topical composition of bemiparin sodium and a topical composition of fondaparinux sodium, a topical composition of non-fractionated heparin are administered to them.

Figure 8:
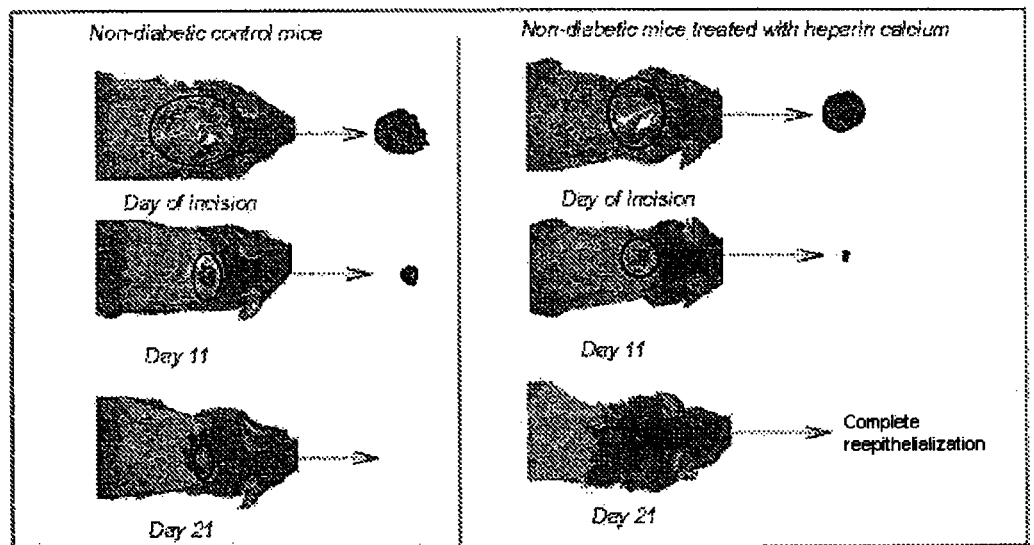

FIG. 8 shows the evolution of the non-diabetic control mice of Example 5 with respect to the mice treated with heparin calcium. The wound area has been depicted to the right of each animal.

Figure 9:
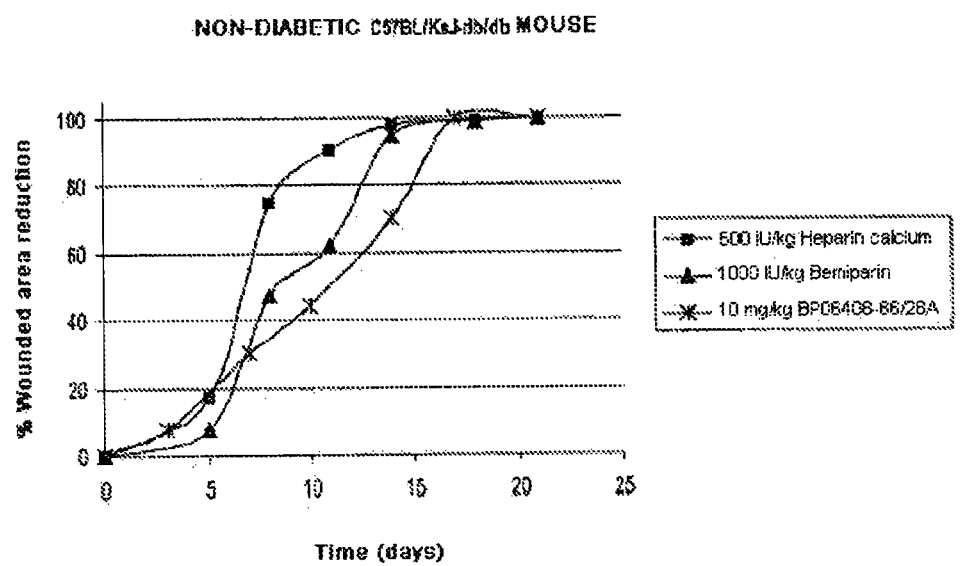

FIG. 9 shows the evolution of the percentage of healing of the wound over time in the mice of Example 5.

Figure 10:
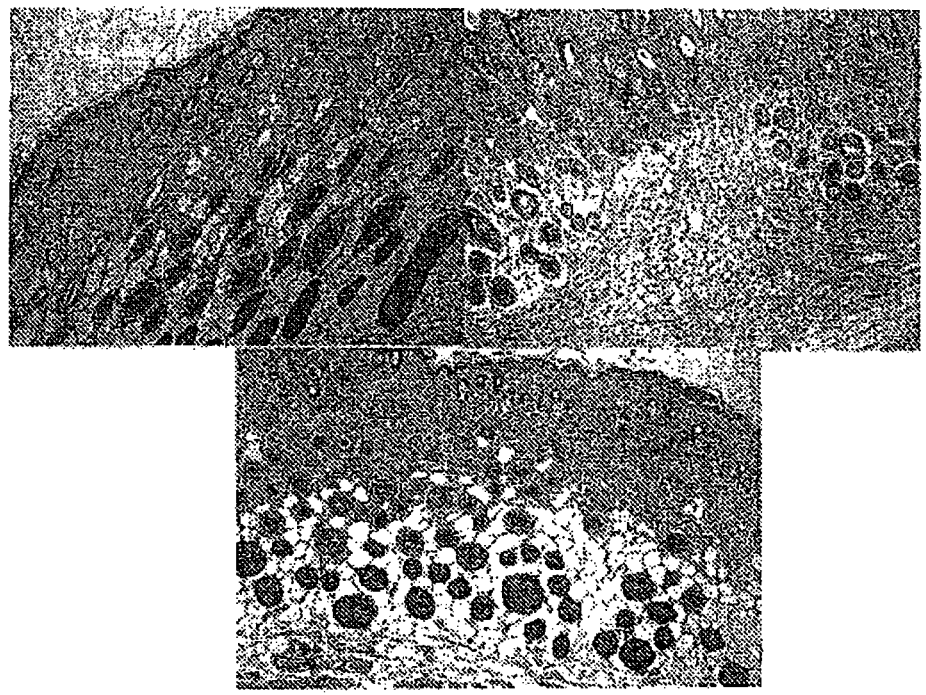

FIG. 10 shows microphotographs of the wound sections of the mice of Example 5 after the staining with hematoxylin-eosin. A non-diabetic control. B non-diabetic animal treated with bemiparin sodium, C non-diabetic animal treated with heparin calcium.

Figure 11:
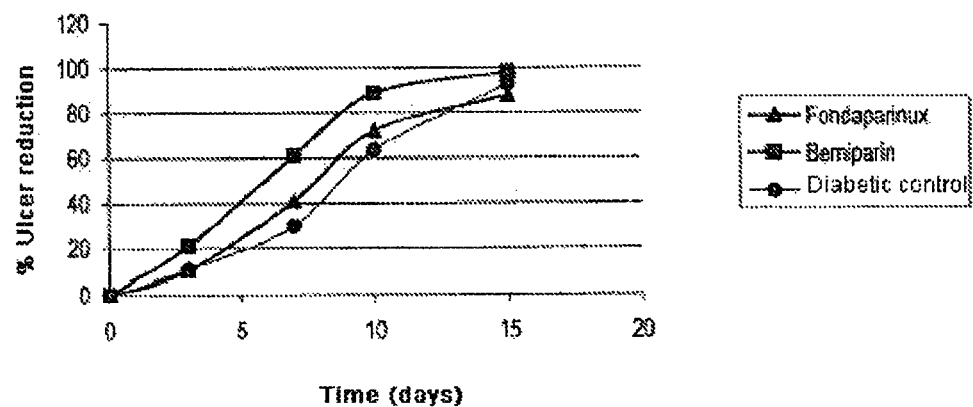

FIG. 11 depicts the percentage of ulcerated area reduction in diabetic wistar rat when a control solution by oral route, an oral 100 mg/kg bemiparin sodium suspension and a 10 mg/kg fondaparinux sodium suspension are administered to it.

Figure 12:
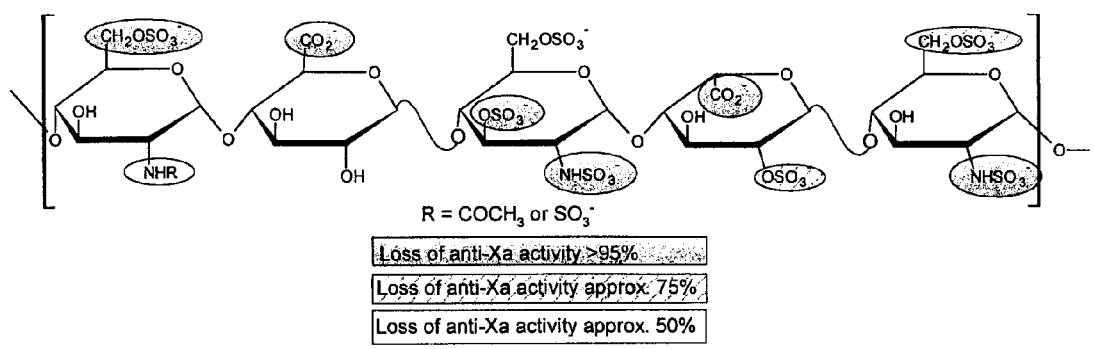

FIG. 12 depicts the pentasaccharide of Formula 1 with indications as to the loss of anti-Xa activity for elimination of respective functional groups.

DETAILED DESCRIPTION OF THE INVENTION

The problem to be solved by the present invention is, therefore, to provide a pharmaceutical composition solving the problems of the prior art.

The solution is based on the fact that the inventors have identified that a pharmaceutical composition of glycosaminoglycans by subcutaneous or parenteral route, oral route and/or topical route, particularly LMWHs and VLMWHs, for the treatment of chronic ulcers such as diabetic foot ulcers, containing the following proportion of the following monosaccharides (in which all the percentages are over the total percentage of monosaccharides of the composition):
 a) N-sulfo-D-glucosamine: 25-50%
 b) D-glucuronic acid: 3-25%
and characterized in that the proportion of the disaccharide unit D-glucuronic acid bound to N-sulfo-3-sulfo-D-glucosamine is not greater than 25%, and preferably not greater than 20%, achieves solving the indicated problem, since it achieves tissue regeneration, preventing the amputation of the limb, and is effective as therapeutic treatment and not only in prophylaxis.

Another aspect of the invention also relates to the use of a composition of glycosaminoglycans by subcutaneous or parenteral route, oral route and/or topical route, particularly LMWHs and VLMWHs, containing a characteristic proportion of at least the monosaccharides selected from the group N-sulfo-D-glucosamine, N-acetyl-D-glucosamine, L-iduronic acid, 2-sulfated L-iduronic acid and D-glucuronic acid in the manufacture of an alternative medicinal product for the treatment of chronic ulcers such as pressure ulcers and diabetic foot ulcers.

The solution is based on the fact that the inventors have identified that, contrary to the general belief, it is possible to administer to a patient suffering from diabetic foot ulcer a treatment consisting of a dose of low molecular weight heparin (LMWH) classified as venous thromboembolic disease treatment dose without there being a greater bleeding risk, and better results than if it is administered at lower concentrations such as the usual concentrations for prophylaxis being surprisingly obtained, due to the presence of a certain proportion of certain monosaccharides in the glycosaminoglycans. Therefore, the present invention provides a pharmaceutical composition for the treatment of diabetic foot ulcer using the usual treatment doses for venous thromboembolic disease, understanding treatment doses as those in which the ratio between the plasma half-life and the dose in IU of the LMWH is between 1:800 and 1:5,000, i.e., those containing a larger amount of specific monosaccharides.

In a particular embodiment of the present invention, there is provided a pharmaceutical composition of glycosaminoglycans by subcutaneous or parenteral route, oral route and/or topical route, particularly LMWHs and VLMWHs, for the treatment of diabetic foot ulcer containing the following proportion of the following monosaccharides:
 N-sulfo-D-glucosamine: 25-50%
 N-acetyl-D-glucosamine: 0-10%
 L-iduronic acid: 0-35%
 2-sulfated L-iduronic acid: 0-50%
 D-glucuronic acid: 3-25%

In another particular embodiment of the present invention, there is provided a pharmaceutical composition of glycosaminoglycans by subcutaneous or parenteral route, oral route and/or topical route, particularly LMWHs and VLMWHs, for the treatment of diabetic foot ulcer containing the following proportion of the following monosaccharides:
 N-sulfo-D-glucosamine: 25-50%
 N-acetyl-D-glucosamine: 0-10%
 L-iduronic acid: 0-10%
 2-sulfated L-iduronic acid: 15-50%
 D-glucuronic acid: 3-25%

In another particular embodiment of the present invention, there is provided a pharmaceutical composition of glycosaminoglycans by subcutaneous or parenteral route, oral route and/or topical route, particularly LMWHs and VLM- WHs, for the treatment of diabetic foot ulcer containing the following proportion of the following monosaccharides:
N-sulfo-D-glucosamine: 25-50%
N-acetyl-D-glucosamine: 0.1-8%
L-iduronic acid: 1-10%
2-sulfated L-iduronic acid: 15-40%
D-glucuronic acid: 3-15%

More particularly, the present invention is aimed at a pharmaceutical composition of glycosaminoglycans by subcutaneous or parenteral route, oral route and/or topical route, particularly LMWHs and VLMWHs, for the treatment of chronic ulcers such as diabetic foot ulcers, containing a proportion of the disaccharide unit D-glucuronic acid bound to N-sulfo-3-sulfo-D-glucosamine ($A_{NS,3S}$) less than 20%, even more preferably less than 10% and most preferably less than 5% of the total saccharide composition.

One of the merits of this invention is not only having eliminated a prejudice of the state of the art, but also achieving an effective correlation between the proportion of the aforementioned monosaccharides with the dose of medicinal product containing the aforementioned pharmaceutical composition necessary for treating the diabetic foot ulcer as well as for favoring tissue healing and regeneration in the patients according to the plasma half-life of these glycosaminoglycans.

The plasma half-life for various known LMWHs is shown in Table 1, the data of which have been extracted from the publication Planes, A. Review on bemiparin sodium—a second generation low molecular weight heparin—and its applications in venous thromboembolism. Expert opinion Pharmacother. 2003; 4:1551-61.

TABLE 1

| LMWH | Plasma Half-Life Range (hours) | Plasma Half-Life (hours) |
|---|---|---|
| RO-14 | 6.5-6.9 | 6.7 |
| Bemiparin | 5.2-5.4 | 5.3 |
| Enoxaparin | 4.0-4.4 | 4.2 |
| Nadroparin | 3.7 | 3.7 |
| Dalteparin | 2.3-2.8 | 2.5 |
| Tinzaparin | 3.0 | 3.0 |

In relation to the different types of LMWHs, it is observed that the doses used depend in an inversely proportional manner on the plasma half-life, as shown in Table 2 (source: see the aforementioned article of "Expert opinion Pharmacother", except for the case of RO14, the data of which come from experiments of the applicant):

TABLE 2

| LMWH | Average dose (IU/day) | Approximate Half-life/Dose Ratio |
|---|---|---|
| RO-14 | 5,400 | 1:800 |
| Bemiparin | 5,000 | 1:950 |
| Enoxaparin | 8,000 | 1:1,900 |
| Nadroparin | 7,600 | 1:2,000 |
| Dalteparin | 10,000 | 1:4,000 |
| Tinzaparin | 10,000 | 1:3,300 |

As a result, an additional aspect of the invention is aimed at the use of glycosaminoglycans, particularly low molecular weight heparins, in the manufacture of a medicinal product for the treatment of diabetic foot ulcer which is characterized in that the ratio between the plasma half-life and the dose in IU of the LMWH is between 1:800 and 1:5,000, i.e., it is characterized in that a composition containing a larger amount of the monosaccharides selected from the group consisting of N-sulfo-D-glucosamine, N-acetyl-D-glucosamine and D-glucuronic acid, and in preferred embodiments of the invention also L-iduronic acid and 2-sulfated L-iduronic acid, and a proportion of the disaccharide unit D-glucuronic acid bound to N-sulfo-3-sulfo-D-glucosamine less than 20% of the total saccharide composition, for the treatment of diabetic foot ulcer, more preferably less than 10% and most preferably less than 5%, is administered.

In another aspect, the invention is aimed at the use of a low molecular weight heparin in the manufacture of a medicinal product for the treatment of diabetic foot ulcer in which the LMWH is a heparin with an average molecular weight less than 6,000 daltons.

In another aspect, the invention is aimed at the use of a low molecular weight heparin in the manufacture of a medicinal product for the treatment of diabetic foot ulcer characterized in that the plasma half-life is between 5.2 and 5.4 and the daily average dose is 5,000 IU, which ensures having a specific proportion of the monosaccharides selected from the group consisting of N-sulfo-D-glucosamine and D-glucuronic acid, and in preferred embodiments of the invention also N-acetyl-D-glucosamine, L-iduronic acid and 2-sulfated L-iduronic acid, and the disaccharide unit G-glucuronic acid bound to N-sulfo-3-sulfo-D-glucosamine less than 20% of the total saccharide composition, more preferably less than 10% and most preferably less than 5%

In another aspect, the invention is aimed at the use of a low molecular weight heparin in the manufacture of a medicinal product for the treatment of diabetic foot ulcer characterized in that the plasma half-life is between 4.0 and 4.4 and the daily average dose is 7,600 IU, which ensures having a specific proportion of the monosaccharides selected from the group consisting of N-sulfo-D-glucosamine, N-acetyl-D-glucosamine, L-iduronic acid, 2-sulfated L-iduronic acid and D-glucuronic acid.

In another aspect, the invention is aimed at the use of a low molecular weight heparin in the manufacture of a medicinal product for the treatment of diabetic foot ulcer characterized in that the plasma half-life is between 2.3 and 2.8 and the daily average dose is 10,000 IU, which ensures having a specific proportion of the monosaccharides selected from the group consisting of N-sulfo-D-glucosamine and D-glucuronic acid, and in preferred embodiments of the invention also N-acetyl-D-glucosamine, L-iduronic acid and 2-sulfated L-iduronic acid.

As has been indicated, as a result of providing an LMWH at a treatment dose in which the ratio between the plasma half-life of each LMWH and the dose in IU of each LMWH is between 1:800 and 1:5,000, the advantage of providing an alternative medicinal product for the treatment of chronic ulcers such as diabetic foot ulcers giving a greater effectiveness than traditional treatments is achieved without a significant increase of the drawbacks typically associated with this treatment, such as a greater bleeding risk, due to the fact that it contains a larger amount of certain monosaccharides and a limited amount of the disaccharide unit D-glucuronic acid bound to N-sulfo-3-sulfo-D-glucosamine less than 20% of the total saccharide composition.

This invention has been possible as a result of the fact that the inventors have overcome the prejudice existing in the technical field of heparins against raising the concentration of LMWHs to levels in the order of the venous thromboembolic disease treatment doses, instead of remaining in the usual (lower) prophylactic doses, in the belief that such raising would significantly increase the bleeding risk without causing beneficial effects in relation to the improvement of epithelial tissue regeneration and healing, as observed in the present invention.

Furthermore, without wishing to be bound by theory, the inventors of the present invention consider, however, that the results of the examples support their hypothesis, since if the synthetic pentasaccharide (fondaparinux) is used for the treatment of diabetic foot ulcer, the healing and/or regenerative activity is highly reduced (when it should be the reverse) in the same manner as if the monosaccharides selected from the group consisting of N-sulfo-D-glucosamine, N-acetyl-D-glucosamine, L-iduronic acid, 2-sulfated L-iduronic acid and D-glucuronic acid are chemically and/or enzymatically modified, the activity of the composition of glycosaminoglycan decreases drastically. It is therefore concluded that although there is a pentasaccharide portion in the structure, it is not responsible for the tissue healing and/or regenerative activity, as well as if the aforementioned monosaccharides are qualitatively or quantitatively altered, a good tissue healing and/or regenerative activity is not obtained.

EXAMPLES

The following specific examples provided below serve to illustrate the nature of the present invention. These examples are only included for illustrative purposes and must not be interpreted as limitations to the invention claimed herein.

A series of experiments have been conducted to demonstrate that the use of glycosaminoglycans such as low molecular weight heparins in the manufacture of medicinal products for the treatment of diabetic foot ulcer at treatment doses for LMWHs in which the ratio between the plasma half-life of each LMWH and the dose in IU of the LMWH is between 1:800 and 1:5,000 provide the indicated advantages of the invention.

Several compounds have been used in these experiments, particularly the following:
Commercial Products:
Fondaparinux:
Pentasaccharide analog with high affinity for antithrombin III obtained by chemical synthesis. It has the following characteristics, among others: Molecular weight of 1728 Daltons and an anti-factor Xa activity: 700 IU/mg.

Bemiparin:
it is a second generation heparin, with a low molecular weight (average molecular weight of 3,600 daltons) and an anti-Xa/anti-IIa ratio greater than 8. Bemiparin is obtained by a new depolymerization and fractionation—beta-elimination in a non-aqueous medium—method for the purpose of achieving an even lower molecular weight than the previous heparins, as well as an optimal distribution of the fragments thereof, such that the resulting percentage of fragments of more than 6,000 Daltons is much lower than the rest of the LMWHs, with a high proportion of chains below the critical length (MW<5,400 D). Without wishing to be bound by theory, the inventors believe that it is precisely the monosaccharides present which do not form part of the characteristic portion of the pentasaccharide responsible for the antithrombotic activity, which are considered secondary and which were not considered important to date, which provide the LMWHs of the invention with the indicated advantages, for this reason, the greater the dose of these monosaccharides, the better the healing and curing of the diabetic foot ulcers.

Enoxaparin:
Low molecular weight heparin obtained by depolymerization by a β-elimination method in an aqueous medium of the previously formed benzyl esters of heparin. It has the following characteristics, among others (Ph. Eur. 6th Edition): Average molecular weight of 3500-5500 Daltons and an anti-factor Xa activity: 90-125 IU/mg Dalteparin:
Low molecular weight heparin obtained by depolymerization with nitrous acid. It has the following characteristics, among others (Ph. Eur. 6th Edition): Average molecular weight of 5600-6400 Daltons and an anti-factor Xa activity: 110-210 IU/mg Tinzaparin:
Low molecular weight heparin obtained by enzymatic depolymerization with heparinase I. It has the following characteristics, among others (Ph. Eur. 6th Edition): Average molecular weight 5500-7500 Daltons and an anti-factor Xa activity: 70-120 IU/mg.

Heparin Sodium:
Non-fractionated heparin. It has the following characteristics, among others (Ph. Eur. 6th Edition): Anti-coagulating activity: ≥150 IU/mg Heparin Calcium:
Non-fractionated heparin. It has the following characteristics, among others (Ph. Eur. 6th Edition): Anti-coagulating activity: ≥150 IU/mg Products in Investigational Phase:
RO-14:
Very low molecular weight heparin obtained by depolymerization by a β-elimination method in a non-aqueous medium. It has the following characteristics, among others: Average molecular weight of 1800-3000 Daltons and it has an anti-factor Xa activity: 80-140 IU/mg.

BEMI-99/4:
It is a low molecular weight heparin having the degree of sulfation altered, such that it only has sulfate groups in position N of the glucosamines. For this reason, its anti-factor Xa activity decreases considerably because the pentasaccharide portion is qualitatively and quantitatively affected.

The modifications for obtaining this heparin are based on a reaction of de-N,O-sulfation which is carried out according to the conditions described by Nagasawa and Inoue (Nagasawa K, Inoue Y. De-N-sulfation. Methods Carbohydr. Chem. 1980; 8:287-289) and of N-sulfation, according to the conditions of Lloyd et al. Lloyd A G, Embrey G, Fowler L J. Studies on heparin degradation-I: Preparation of [35S] sulphamate derivatives for studies on heparin degrading enzymes of mammalian origin. Biochem. Pharmacol. 1971; 20:637-648), thus 10 g of bemiparin are dissolved in 150 ml of water and the solution is passed through a Dowex 50WX8,H+ column. The eluate is neutralized with pyridine and lyophilized, 11.2 g of bemiparin pyridinium salt being obtained.

The bemiparin pyridinium salt (3 g) is dissolved in 75 ml of dimethylsulfoxide containing 10% methanol, and the solution is maintained for 24 hours at 105° C. After this time, 75 ml of water are added, the pH is adjusted to 9.0-9.5 with sodium hydroxide and it is stirred for 15 minutes. The solution is neutralized with hydrochloric acid, 0.5 g of sodium chloride are dissolved and it is precipitated with the addition of 3 volumes of methanol, the de-N,O-sulfated derivative being obtained.

The de-N,O-sulfated derivative (1 g) is N-sulfated, according to the conditions of Lloyd et al. The product is dissolved in 75 ml of a saturated sodium bicarbonate solution and the pH is adjusted to 9. The solution is heated to 55° C. and 3 g of sulfur trioxide-trimethylamine complex are added. The reaction is maintained for 3 hours at 55° C. After this time, 3 g of sulfur trioxide-trimethylamine complex are added again, leaving the reaction at 55° C. for another 3 hours. The solution is cooled and the pH is adjusted to 7 with hydrochloric acid, 1 g of sodium chloride is added and it is precipitated with three volumes of methanol. 0.88 g of BEMI-99/4 are obtained. The product obtained has the following characteristics: Average molecular weight of 3468 Daltons and an anti-factor Xa activity: 4 IU/mg.

BEMI-99/2:

It is a low molecular weight heparin having the degree of sulfation altered by a de-N-sulfation reaction. This involves a decrease in its anti-factor Xa activity because the pentasaccharide is affected.

The modifications for obtaining this heparin are based on the conditions described by Nagasawa and Inoue (Nagasawa K, Inoue Y. De-N-sulfation. Methods Carbohydr. Chem. 1980; 6:287-289).

3 g of bemiparin pyridinium salt (prepared as indicated in the previous example) are dissolved in 450 ml of dimethylsulfoxide containing 10% methanol, and the solution is maintained for 2 hours at 55° C. After this time, the pH is adjusted to 9.0-9.5 with sodium hydroxide and it is stirred for 15 minutes. The solution is neutralized with hydrochloric acid, 0.5 g of sodium chloride are dissolved and it is precipitated with the addition of 3 volumes of methanol, the de-N,O-sulfated derivative being obtained. 0.91 g of BEMI-99/2 are obtained. The product obtained has the following characteristics: Average molecular weight of 3619 Daltons and an anti-factor Xa activity: 19 IU/mg.

H13-96/5:

It is a low molecular weight heparin having a lower degree of acetylation. For this reason, its anti-factor Xa activity decreases considerably because the pentasaccharide portion is qualitatively and quantitatively affected.

In this case, to be able to obtain this glycosaminoglycan, a de-N-acetylation is carried out according to the conditions described by Shaklee and Conrad (Shaklee P N, Conrad H E. Hydrazinolysis of heparin and other glycosaminoglycans. Biochem J 1984; 217:187-197). Thus, 5 g of RO-14 are dissolved in 125 ml of anhydrous hydrazine containing 1% hydrazine sulfate and maintained for 6 hours at 95° C. The solution is concentrated to dryness, redissolved in the minimum amount of water and neutralized with hydrochloric acid. 2.5 g of sodium chloride are added and it is precipitated with 3 volumes of methanol, the product H13-96/5 (3.4 g) being obtained. The product obtained has the following characteristics: Average molecular weight of 2008 Daltons and an anti-factor Xa activity: 46 UI/mg.

BP06408-66/27-A:

It is a low molecular weight heparin with reduced anti-factor Xa activity, obtained by the fractionation of bemiparin by affinity chromatography on ATIII.

To obtain this derivative, 10 mg of bemiparin are passed through a CNBr-activated Sepharose 4B column previously activated with (human) ATIII, prepared according to the conditions described by HööK et al. (Höök M, Björk I, Hopwood J, Lindahl U. FEBS Lett. 1976; 66:90-93). The column is eluted at 4° C. with a pH 7.40 buffer solution of 1 mM Tris-HCl+0.4 M NaCl, the fraction with low affinity thus being eluted.

This fraction is purified by a Biogel P2 column, eluting with water. The solution containing the product is lyophilized, 7.6 mg of product finally being obtained.

The product obtained has the following characteristics: Average molecular weight of 3567 Daltons and an anti-factor Xa activity: 32 IU/mg.

BP06408-66/28-A:

It is a low molecular weight heparin with minimized anti-factor Xa activity, obtained by the fractionation of bemiparin by affinity chromatography on ATIII.

To obtain this derivative, 10 mg of bemiparin are passed through the affinity column described in the preparation of the previous product. The column is eluted at 4° C. with a pH 7.40 buffer solution of 1 mM Tris-HCl+0.25 M NaCl, the fraction with low affinity being eluted.

This fraction is purified by a Biogel P2 column, eluting with water. The solution containing the product is lyophilized, 3.6 mg of product finally being obtained.

The product obtained has the following characteristics: Average molecular weight of 3611 Daltons and an anti-factor Xa activity: 5.4 IU/mg.

The experiments conducted were generally the following: preparation and quantification and identification of fractions of the glycosaminoglycan fractions by means of NMR and administration in previously diabetized wistar rats and in genetically modified mice to assess the healing of said ulcers.
Study of Quantification and Identification of Fractions by NMR
Determination of the Monosaccharide Proportions of the Products The inventors of the present invention have analyzed commercial samples and their own research samples, to determine the monosaccharide proportions of those monosaccharides responsible for the healing of diabetic foot ulcer as well as the different saccharide fractions present in the pentasaccharide.

The average content of monosaccharides in the glycosaminoglycan (GAG) samples has been determined by means of the Nuclear Magnetic Resonance (NMR) technique, using quantitative $^{13}C$-$^{1}H$ HSQC (heteronuclear single quantum coherence) two-dimensional experiments, according to the method described by Marco Guerrini et al. The increase of resolution which is achieved with the second dimension allows quantifying signals which overlap in the one-dimensional spectrum, this technique being of special interest to study complex carbohydrates such as GAGs. These molecules have serious overlap problems in one-dimensional 1H spectra which make it difficult to determine the areas of isolated peaks in 1D for their quantification.

The amount of the unit of D-glucuronic acid bound to N-sulfo-3-sulfo-D-glucosamine G(ANS,3S) present in GAGs obtained from natural heparin can be directly related to the anti-Xa activity thereof, as described by M. Guerrini et al. This disaccharide belongs to the pentasaccharide responsible for the interaction with antithrombin III and is only detected in the active sequences. The correlation signal of the anomeric carbon of this type of glucuronic acid with the directly bound hydrogen appears in a characteristic and overlap-free region in the HSQC spectrum and can therefore be used to quantify the proportion of the pentasaccharide in the GAG.

The $^{13}C$-$^{1}H$ HSQC spectra of fondaparinux and of different GAGs are shown in attached FIGS. 2A to 2L, in which the $^{1}H$-$^{13}C$ correlation signal of the anomeric proton corresponding to the unit of glucuronic acid of the pentasaccharide has been highlighted with a circle.

The measurement of the intensity of this signal in the spectra allows determining the proportion of pentasaccharide. The results indicate that the percentage of the monosaccharide G-(ANS,3S) in no case exceeds 3% in the GAGs analyzed, unlike fondaparinux in which the proportion is 20%.

However, the GAGs studied have new monosaccharide units, such as non-sulfated iduronic acid rings (I) or N-acetylated glucosamines (ANAc). Likewise, the proportion of the unit of 2-sulfated iduronic acid is much greater than in the pentasaccharide. Therefore, the samples analyzed contain mostly oligosaccharide chains different from fondaparinux.

| Fractions | Fondaparinux | Bemiparin | RO14 | H13_96_5 | BEMI_99_2 | BEMI_99_4 | BP0640866/27A | BP0640866/28A | Enoxaparin | Dalteparin | Tinzaparin | Non-fractionated heparin | % |
|---|---|---|---|---|---|---|---|---|---|---|---|---|---|
| ANS | 40 | 44.4 | 35.3 | 39.6 | — | 44.4 | 43.4 | 49.3 | 40.65 | 37.3 | 42.45 | 42.6 | 25-50 |
| ANAc | 0 | 2.9 | 2.2 | 0.1 | 2.5 | 6.03 | 1.8 | 4.1 | 5.6 | 5.15 | 7.5 | 5.1 | 0-10 |
| I2S | 20 | 30.7 | 28.3 | 23.1 | 26.9 | 0 | 34.6 | 22.6 | 26 | 37.7 | 30.2 | 38.4 | 0-50 |
| I | 0 | 2.8 | 3.3 | 1.4 | 1.8 | 34.2 | 1.8 | 1.3 | 3.35 | 5.0 | 4.30 | 5.7 | 0-35 |
| G | 20 | 5.7 | 5.7 | 6.8 | 5.7 | 9.26 | 6.2 | 8.6 | 8.4 | 7.25 | 7.9 | 7.0 | 3-25 |
| $A_{NS,3S}$ | 20 | 2.4 | 3.1 | 3.0 | 0 | 0 | <0.1 | 0 | 2.2 | 2.3 | 1.0 | 2.2 | <20 |
| G-$A_{NS,3S}$ | 20 | 1.5 | 2.6 | 1.9 | 0 | 0 | <0.1 | 0 | 1.7 | 2.05 | 1.05 | 1.0 | <20 |

All the data in this table are expressed in %
ANS: N-sulfo-D-glucosamine
ANAc: N-acetyl-D-glucosamine
I2S: 2-sulfated L-iduronic acid
I: L-iduronic acid
G: D-glucuronic acid
$A_{NS,3S}$: N-sulfo-3-sulfo-D-glucosamine
G-$A_{NS,3S}$: D-glucuronic acid bound to N-sulfo-3-sulfo-D-glucosamine Study in Wistar Rat by Parenteral Route Example 1

Diabetization of Wistar Rats

To perform the present example, doses of 45 mg/kg of streptozocin (STZ) were administered by intramuscular route to make a batch of 8 rats diabetic (Andrades Ja et al. Engineering, expression, and renaturation of a collagen-targeted human bFGF fusion protein. Growth Factors. 2001; 18(4): 261-75).

Male wistar rats with an average weight of 250 g per rat were used, to which a dose of 11.25 mg STZ per rat was administered by means of the intramuscular administration of 100 µL in the left paw of each rat.

Sweetened water (350 mg/dL) was administered to all the rats for three days and glucose measurements were performed with a glucometer every day to verify that the rats were indeed diabetized. For this reason, before the administration and at time 4 days after the administration of streptozocin, a drop of blood was extracted from the rat tail vein for the subsequent quantification of glycemia and to see whether they were diabetic before starting the ulceration assay.

TABLE 1

Weight-glycemia measurement of wistar rats

| RAT | WEIGHT (g) | Glycemia Day 0 (mg/dL) | Glycemia Day 4 (mg/dL) | Glycemia Day 9 (mg/dL) |
|---|---|---|---|---|
| 1 | 250 | 120 | >350 | >350 |
| 2 | 245 | 129 | >350 | — |
| 3 | 255 | 119 | >350 | — |
| 4 | 250 | 135 | >350 | — |
| 5 | 240 | 136 | >350 | — |
| 6 | 260 | 171 | >350 | >350 |
| 7 | 270 | 124 | >350 | — |
| 8 | 245 | 133 | >350 | — |

Ulceration of Wistar Rats and Measurement of the Degree of Healing

For this example, 3 groups with 8 male Wistar rats in total were chosen:

| | |
|---|---|
| Control group: | 2 rats |
| Group 1: High dose of heparin (217 IU) | 3 rats |
| Group 2: Low dose of heparin (108 IU) | 3 rats |

The selection of the rats included in each group was performed randomly.

Once the rats were diabetized, 4 ulcers with a diameter of 1 cm each were made on them using a scalpel. An anesthesia/analgesia protocol with Ketamine/xylazine was followed according to the recommendations of the book: "Handbook of laboratory animal management and welfare":

Anesthesia: 10 mg/kg xylazine+90 mg/kg ketamine IP
Analgesia: 300 mg/kg paracetamol by oral route (dissolved in water)

In the present example, on the day after the ulceration all the rats included in the study except one from Group 1 and another one from Group 2 were dead. The cause of the death was not due to infection phenomena, but rather it was possibly due to the effect of the anesthesia. Therefore, the experiment was continued with two rats with four ulcers each, one with a high dose of bemiparin and another one with a low dose of bemiparin, therefore the experiment was continued to observe differences in the healing and ulcerated surface between the different doses.

The ulcers were treated with water and cleaned for 9 days after the ulceration.

The administrations of bemiparin were performed by means of a bemiparin solution by subcutaneous route (100 µL) for the treatment of the ulcers.

The diameter of the ulcer was quantified by means of tracing the ulcer onto a transparency to see the progress of the healing.

Table 2 shows the calculation of the percentage of area reduction of day 9 with respect to day 1:

TABLE 2

| 108 IU Rat | | 217 IU Rat | |
|---|---|---|---|
| E | 43.23%* | A | 26.2% |
| F | 17.36% | B | 20.14% |

TABLE 2-continued

| | 108 IU Rat | | 217 IU Rat |
|---|---|---|---|
| G | 32.24% | C | 25.64% |
| H | 23.59% | D | 37.43% |
| Average: | 24.39 ± 7.47 | Average: | 27.35 ± 7.25 |

(*It is excluded from the average due to erroneous quantification)

Progress of the Healing

Quantitatively, not much difference is seen in relation to the area of the ulcers between the two rats. However, the healing process of the D=217 IU rat is macroscopically much better since the closure of the ulcer had higher quality in the granulation or dermal tissue regeneration with less fibrous content than the D=108 IU rat, therefore a qualitative improvement is seen in relation to the ulcerated tissue healing and regeneration with the D=217 administration.

Example 2

Diabetization of Wistar Rats

To perform the present embodiment, doses of 45 mg/kg of streptozocin (STZ) were administered by intramuscular route to make a batch of 8 rats diabetic (Andrades Ja et al. Engineering, expression, and renaturation of a collagen-targeted human bFGF fusion protein. Growth Factors. 2001; 18(4): 261-75).

Male wistar rats with a average weight of 250 g per rat were used, to which a dose of 11.25 mg STZ per rat was administered by means of the intramuscular administration of 100 µL in the left paw of each rat.

Sweetened water (350 mg/dL) was administered to all the rats for three days and glucose measurements were performed with a glucometer every day to verify that the rats were indeed diabetized. For this reason, before the administration and at time 4 days after the administration of streptozocin, a drop of blood was extracted from the rat tail vein for the subsequent quantification of glycemia and see whether they were diabetic before starting the ulceration assay.

TABLE 3

Weight-glycemia measurement of wistar rats

| RAT | WEIGHT (g) | Glycemia Day 0 (mg/dL) | Glycemia Day 4 (mg/dL) | Glycemia Day 9 (mg/dL) |
|---|---|---|---|---|
| 1 | 240 | 128 | >350 | 1 |
| 2 | 240 | 132 | >350 | 2 |
| 3 | 250 | 121 | >350 | 3 |
| 4 | 260 | 138 | >350 | 4 |
| 5 | 250 | 142 | >350 | 5 |
| 6 | 245 | 136 | >350 | 6 |
| 7 | 265 | 129 | >350 | 7 |
| 8 | 245 | 141 | >350 | 8 |

Ulceration of Wistar Rats and Measurement of the Degree of Healing

For this example, 3 groups with 8 male Wistar rats in total were chosen:

| Control group Fondaparinux | 2 rats |
|---|---|
| Group1: High dose of heparin (217 IU) | 2 rats |
| Group2: Low dose of heparin (108 IU) | 2 rats |

The selection of the rats included in each group was performed randomly.

Once the rats were diabetized, 2 ulcers with a diameter of 1 cm each were made on them using a scalpel. An anesthesia/analgesia protocol with ketamine/xylazine was followed according to the recommendations of the book: "Handbook of laboratory animal management and welfare":

Anesthesia: 10 mg/kg xylazine+90 mg/kg ketamine IP
Analgesia: 300 mg/kg paracetamol by oral route (dissolved in water)

The ulcers were treated with water and cleaned for 9 days after the ulceration.

The administrations of bemiparin and of fondaparinux were performed by means of a bemiparin solution by subcutaneous route (100 µL) for the treatment of the ulcers.

The diameter of the ulcer was quantified by means of tracing the ulcer onto a transparency to see the progress of the healing.

Table 4 shows the calculation of the percentage of area reduction of day 9 with respect to day 1:

TABLE 4

| | 217 IU Rats Batch 1 | | 108 IU Rats Batch 2 | | Fondaparinux Rats Batch 3 |
|---|---|---|---|---|---|
| A | 29.31% | E | 16.96% | H | 17.00%* |
| B | 31.85% | F | 13.26% | I | 20.69% |
| C | 28.40% | G | 19.14% | J | 21.32% |
| D | 24.89% | H | 19.71% | K | 23.81% |
| Average: | 27.35 ± 7.25 | Average: | 24.39 ± 7.47 | Average: | 20.70 ± 7.20 |

The averages of the three batches of this assay are shown in FIG. 3.

Progress of the Healing

In this assay, an ulcerated area reduction already appears between day 0 to day 9 (see FIG. 3); furthermore, as in Example 1, a macroscopically quantitative difference with respect to the type of healing of the ulcerated tissue is indeed seen: the healing process of the D=217 IU rat is macroscopically much better than in the case of fondaparinux, in which the wound had hardly variation on day 9 with respect to day 0. In the case of the rat with D=217, the closure of the ulcer had higher quality in the granulation or dermal tissue regeneration with less fibrous content which the rat D=108 IU, therefore a qualitative improvement is seen in relation to the ulcerated tissue healing and regeneration with the D=217 administration and the rat with fondaparinux.

Example 3

Diabetization of Wistar Rats

To perform the present embodiment, doses of 45 mg/kg of streptozocin (STZ) were administered by intramuscular route to make a batch of 10 rats diabetic (Andrades Ja et al. Engineering, expression, and renaturation of a collagen-targeted human bFGF fusion protein. Growth Factors. 2001; 18(4): 261-75).

Male wistar rats with an average weight of 250 g per rat were used, to which a dose of 11.25 mg STZ per rat was administered by means of the intramuscular administration of 100 µL in the left paw of each rat.

Diabetes was induced in 6 of all the rats and 4 of them were left as a non-diabetic control, to test the result of the healing of chronic ulcers not caused by diabetes.

Sweetened water (350 mg/dL) was administered to the rats for three days and glucose measurements were performed with a glucometer every day to verify that the rats were indeed diabetized. For this reason, before the administration and at time 4 days after the administration of streptozocin, a drop of blood was extracted from the rat tail vein for the subsequent quantification of glycemia and see whether they were diabetic before starting the ulceration assay.

TABLE 5

Weight-glycemia measurement of wistar rats

| RAT | WEIGHT (g) | Glycemia Day 0 (mg/dL) | Glycemia Day 4 (mg/dL) |
|---|---|---|---|
| 1 | 250 | 138 | >350 |
| 2 | 255 | 145 | >350 |
| 3 | 250 | 129 | >350 |
| 4 | 260 | 122 | >350 |
| 5 | 255 | 146 | >350 |
| 6 | 260 | 140 | >350 |
| NON-DIABETIC RATS | | | |
| 7 | 245 | 135 | 141 |
| 8 | 260 | 149 | 137 |
| 9 | 245 | 152 | 129 |
| 10 | 250 | 148 | 138 |

Ulceration of Wistar Rats and Measurement of the Degree of Healing

For this example, 5 groups with 10 male Wistar rats in total were chosen:

| | |
|---|---|
| Non-diabetic control group | 2 rats |
| Diabetic control group | 2 rats |
| Group1: Non-diabetic Bemiparin (217 IU/rat) | 2 rats |
| Group2: Diabetic Bemi 99_2 (2.2 mg/rat) | 2 rats |
| Group3: Diabetic fondaparinux (0.22 mg/rat) | 2 rats |

The selection of the rats included in each group was performed randomly.

Once the rats are ready, 2 ulcers with a diameter of 1 cm each were made on them using a scalpel. An anesthesia/analgesia protocol with ketamine/xylazine was followed according to the recommendations of the book: "Handbook of laboratory animal management and welfare":

Anesthesia: 10 mg/kg xylazine+90 mg/kg ketamine IP

Analgesia: 200 mg/kg ibuprofen by oral route (dissolved in 1 L of water)

In the present example, on the day after the ulceration, one of the diabetic rats of group 3 was dead. The cause of the death was not due to infection phenomena, but rather it was possibly due to the effect of the anesthesia. Therefore, the experiment was continued with 8 rats with two ulcers each of the diabetic control group, non-diabetic control group, group 1 and group 2 and with 1 rat with two ulcers of group 3, therefore the experiment was continued to observe differences in the healing and ulcerated surface between the different doses.

The ulcers were treated with water and cleaned for 9 days after the ulceration. A corresponding solution was administered to each group by SC route (100 µL) for the treatment of the ulcers. The diameter of the ulcer was quantified by means of tracing the ulcer onto a transparency to see the progress of the healing.

Table 6 shows the calculation of the percentage of healing of day 9 with respect to day 1:

TABLE 6

| Non-diabetic control | Group 1 | Diabetic control | Bemi 99_2 | Fondaparinux |
|---|---|---|---|---|
| A 39.85% | A 75.05% | A 56.70% | A 51.98% | A 50.99% |
| B 46.12% | B 69.83% | B 57.24% | B 37.08% | B 49.55% |
| C 51.02% | C 72.56% | C 47.41% | C 68.21% | — |
| D 43.74% | D 69.83% | D 51.82% | D 62.12% | —% |
| Average: 45.18% | Average: 71.82% | Average: 53.29% | Average: 54.85% | Average: 50.22% |

A study of the percentage of healing has been performed in this assay: as can be observed, the rats, in a study process of 9 days, have a percentage of healing of approximately 50%, i.e., in 9 days the wound is reduced to half. However, as observed in the previous examples, when a composition of oligosaccharides with a higher percentage of the monosaccharides:

a) N-sulfo-D-glucosamine: 25-50% b) D-glucuronic acid: 3-25% wherein the proportion of the disaccharide unit D-glucuronic acid bound to N-sulfo-3-sulfo-D-glucosamine is not greater than 20%, is administered to them, it is observed that the healing increases to approximately 70%, and even more if the dose is greater (larger amount in relation to the total of monosaccharides).

In non-diabetic rats, the healing is similar to the diabetized rats. In other words, no difference is observed between the healing of the diabetic controls and the non-diabetic controls.

When fondaparinux is administered to them, the percentage of healing remains equal, i.e., there are no improvements compared to its diabetic control, therefore it is concluded that this product does not really favor the healing of the ulcers.

When the altered low molecular weight heparin Bemi__99__2 is administered, the response is virtually the same as its diabetic control, therefore it is concluded that this product does not really favor the healing of the ulcers due to the fact that it has the monosaccharides responsible for the healing of the ulcers altered.

In the case of the administration of non-diabetic bemiparin (217 IU/rat), i.e., the rats of Group 1, it is observed that the healing is substantially reduced by 71.82% compared to its non-diabetic control, therefore it is concluded that in the case of chronic ulcers of non-diabetic patients (such as pressure ulcers) the administration of an oligosaccharide composition with a higher percentage of the monosaccharides:

a) N-sulfo-D-glucosamine: 25-50% b) D-glucuronic acid: 3-25% wherein the proportion of the disaccharide unit D-glucuronic acid bound to N-sulfo-3-sulfo-D-glucosamine is not greater than 20%, it is observed that the healing of approximately 70%.

As qualitative general conclusions of the studies, it is emphasized that the healing process of the rats of Group 1 is macroscopically much better since the closure of the ulcer had higher quality in the granulation or dermal tissue regeneration with less fibrous content than in the rest of groups.

Study in Wistar Rat by Oral Route

The objective of this study is to evaluate the healing activity of the assay products: fondaparinux sodium and bemiparin after their administration by oral route in the diabetic rat wound model.

Both treatments were administered by oral route at an administration volume of 10 mL/kg. In the case of fondaparinux, a dose of 10 mg/kg was administered and in the case of bemiparin, 100 mg/kg were administered.

The control group only received the carrier used to prepare the assay product. The carrier for the preparation of the assay product is a 1.5% (w/v) bicarbonate solution in water for injections. It was verified that the pH of the formulations prepared was above 8.00.

Diabetization of Wistar Rats

At the beginning of the assay, diabetes mellitus was induced in all the animals. To that end, they received a single intraperitoneal injection of streptozotocin (60 mg/kg, 10 mL/kg). After 72 hours, the establishment of the diabetes was verified by analyzing the blood glucose levels. To that end, animals were anesthetized with isoflurane and 0.8 mL of blood were extracted from the retroorbicular plexus. The animals had to have values of glucose greater than 15 mmol/L. A week after the induction of the diabetes, the wound was made.

The animals were anesthetized (ketamine+xylazine, 90+10 mg/kg, i.m.). Their back was shaved and cleaned with disinfectant (povidone-iodine) and the area where the wound would be made was marked by means of a template to homogenize its position in all the animals.

The wound was made by means of a circular incision with a diameter of approximately 1.5 cm, the skin of the mid-dorsal area being removed. 1 mL/animal of physiological serum was administered by i.p. route after the intervention. For the 7 days after the intervention. Analgesia (paracetamol, 1 mg/mL) was provided in drinking water for the 7 days after the intervention.

On the day after making the wound and for a total of 14 days, the assigned treatments were administered to the animals. The follow-up of the animals was performed, the evolution of the wounds being macroscopically assessed twice a week, by means of digital photography of the wound. The body weight of the animals was also recorded twice a week.

On the day after the last administration, the animals were sacrificed with anesthesia overdose (pentobarbital sodium). The area where the wound was made was extracted. The front half was frozen in liquid nitrogen and stored in a freezer (−80±5° C.) and the rear half was stored in formol for its subsequent histological processing.

Measurement of the Degree of Healing

The wound area was calculated as the percentage of reduction thereof to evaluate the degree of curing thereof, by means of the standardized formula:

$$\% \text{ curing} = \frac{(A_{baseline} - A_{time})}{(A_{baseline})} \times 100$$

The measurement performed immediately after the intervention or incision was used as the baseline area.

Non-Diabetized Rats

On the following day and for a total of 14 days, 10 mg/kg were administered to the animals by oral route.

To that end, the animals were previously homogeneously distributed, according to the body weight, into the following treatment groups, with at least 5 animals per group:

| Treatment | Dose |
|---|---|
| Non-diabetic control | — |
| Rat treated with fondaparinux sodium | 10 mg/kg |
| Rat treated with bemiparin sodium | 100 mg/kg |

On the day after making the wound and for a total of 14 days, the assigned treatments were administered to the animals.

The follow-up of the animals was performed, the evolution of the wounds being macroscopically assessed twice a week, by means of digital photography of the wound. The body weight of the animals was also recorded twice a week.

Measurement of the Wound Area.

The values corresponding to the wound area were not significant. In this case, the rats treated with bemiparin sodium reduced the ulceration area more or less to the same extent as the control animals.

Histopathological Evaluation.

The animals were sacrificed on day 15 of the study and the area of the skin where the wound was caused was stored in formol to perform a histopathological evaluation (hematoxylin-eosin staining).

Each section was given a histological score was given in the grade I to grade V range, where I means uncured wound and V means completely epithelialized wound. The score is based on the degree of cell invasion, the formation of granulation tissue, vascularization and epithelialization.

The histopathological scores obtained for the different groups are shown in the following table:

| Treatment | Score | Grade |
|---|---|---|
| Non-diabetic control | 10.0 | III |
| Diabetic animal treated with fondaparinux sodium | 9.5 | III |
| Diabetic animal treated with bemiparin sodium | 9.0 | III |

All the samples belonging to the animals sacrificed 15 days after the beginning of the treatment had evolved healing activity, with clear presence of granulation tissue, neovascularization and more or less complete reepithelization of the induced skin ulceration.

In this case, all the animals show a more or less identical degree of average healing; however, in the control group and in the group treated with fondaparinux, it is observed that there is a high variability in the data with which the average is calculated. In any case, the 5 animals of the group treated with bemiparin sodium obtained a histological value of 9.0, whereby it is observed that the degree of healing is surprisingly homogeneous.

Furthermore, a much more pronounced scab process is observed in the case of the groups treated with Bemiparin than in the animals treated with fondaparinux. In this sense, it should be emphasized that the formation of scab is essential in the healing process of the wound, since it fulfils the objective of limiting the loss of transdermal water and of acting as a barrier against bacteria and external pathogens, preventing the infection of the wound.

In this example, the rats in which scab has been formed on previous days show, in the histopathological analysis of the scar, that the pattern of the dermis is closer to normality, compared with the wounds of the animals in which scab has not been formed or is smaller. In spite of the fact that, after its drop, the healing area is greater and therefore the measurement is not conclusive compared to the animals in which scab has not been formed. Therefore, the formation of scab is a good indicator of the natural healing process, which in this particular case is only macroscopically observed in the group treated with bemiparin.

Study of the Relationship of the Factor Xa Inhibitory Activity of the Glycosaminoglycan and its Healing Power by Oral Route in Diabetic Rat On the following day and for a total of 14 days, 10 mL/kg were administered to the animals by oral route.

To that end, the animals were previously homogeneously distributed, according to the body weight, into the following treatment groups:

| Treatment | Dose |
|---|---|
| Diabetic control | — |
| Rat treated with fondaparinux sodium | 10 mg/kg |
| Rat treated with bemiparin sodium | 100 mg/kg |

On the day after making the wound and for a total of 14 days, the assigned treatments were administered to the animals.

The follow-up of the animals was performed, the evolution of the wounds being macroscopically assessed twice a week, by means of digital photography of the wound. The body weight of the animals was also recorded twice a week.

Measurement of the Wound Area.

FIG. 11 shows the evolution of the diabetized control rats with respect to the diabetized rats treated with bemiparin sodium and fondaparinux. This graph shows how the rats treated with bemiparin heal much better than those treated with fondaparinux. In relation to the areas of the ulcers, when all the products are compared it is observed how the glycosaminoglycans which have a higher proportion of monosaccharides of the regular region have a beneficial effect on the healing of the wounds.

Histopathological Evaluation.

The animals were sacrificed on day 15 of the study and the area of the skin where the wound was caused was stored in formol to perform a histopathological evaluation (hematoxylin-eosin staining).

Each section was given a histological score in the grade I to grade V range, where I means uncured wound and V means completely epithelialized wound. The score is based on the degree of cell invasion, the formation of granulation tissue, vascularization and epithelialization.

| Grade | Score | Description |
|---|---|---|
| I | 1-3 | Nil to minimum cell accumulation, absence of granulation tissue or epithelial development. |
| II | 4-6 | Fine and immature granulation tissue dominated by inflammatory cells but with few fibroblasts, capillaries or collagen deposition; minimum epithelial migration. |
| III | 7-9 | Moderately thick granulation tissue. It can vary from being dominated by inflammatory cells to greater presence of fibroblasts and collagen deposition, extensive neovascularization, minimum to moderate epithelial migration. |
| IV | 10-12 | Thick and vascular granulation tissue dominated by fibroblasts and extensive collagen deposition, the epithelium covers the wound partially or completely. |
| V | 13-15 | Area corresponding to the totally epithelialized wound, without having, more or less, traces of the wound. |

The histopathological scores obtained for the different groups are shown in the following table:

| Treatment | Score | Grade |
|---|---|---|
| Diabetic control | 10.0 | III |
| Diabetic animal treated with fondaparinux sodium | 9.5 | III |
| Diabetic animal treated with bemiparin sodium | 11.3 | IV |

All the samples belonging to the animals sacrificed 15 days after the beginning of the treatment had evolved healing activity, with clear presence of granulation tissue, neovascularization and more or less complete reepithelialization of the induced skin ulceration.

A more evolved granulation tissue, intense neovascularization, with a higher healing level is observed in the group treated with bemiparin sodium, in addition to a greater homogeneity in the results obtained in all the animals. The hyperglycemic animals treated with bemiparin sodium have shown healing levels that are even greater than those of the normoglycemic control group.

These results are supported by the histological findings upon obtaining a higher healing level in the diabetic animals treated with bemiparin sodium.

Study of Diabetic Foot Ulcer in Diabetic Mouse with Genetically Induced Diabetes by Subcutaneous Route Example 4

Ulceration of the C57BL/KS BKS.Cg-m+Lepr$^{db}$/+ Lepr$^{db}$/J Diabetic Mouse, Measurement of the Degree of Healing and Histological Evaluation The C57BL/KsJ-db/db diabetic mouse has been used as a type II diabetes model having an altered healing, unlike the mouse with diabetes induced by streptozotocin used in the previous examples, which is a type I diabetes model (Michaels, J., et al, db/db mice exhibit severe wound-healing impairments compared with other murine diabetic strains in a silicone-splinted excisional wound model. Wound Repair Regen, 2007. 15(5): p. 665-70). The genetically diabetic mouse develops resistance to insulin and hyperglycemia similar to those observed in adult diabetes. The total thickness wounds made in the back of these animals takes longer in forming the granulation tissue and in closing than the same wounds caused in non-diabetic animals.

On the first day of the assay, the animals were anesthetized (ketamine+xylazine, 100+10 mg/kg, i.m.). The back of the animal was shaved, the area was cleaned with disinfectant and the location of the wound was marked by means of a template to make its position the same in all the animals.

The wound was made by means of a circular incision with a diameter of approximately 1.5 cm, the skin of the mid-dorsal area being removed. A semipermeable dressing was subsequently placed on the wound. 1 mL/animal of physiological serum was administered by i.p. route after the intervention.

Analgesia (paracetamol, 1 mg/mL) was administered in drinking water for the 7 days after the intervention.

The wound area was calculated as the percentage of reduction thereof to evaluate the degree of curing thereof, by means of the standardized formula:

$$\% \text{ curing} = \frac{(A_{baseline} - A_{time})}{(A_{baseline})} \times 100$$

The measurement performed immediately after the intervention or incision was used as the baseline area. On the following day and for a total of 14 days, the assigned treatments were administered to the animals.

Study of the Relationship of the Factor Xa Inhibitory Activity of the Glycosaminoglycan and its Healing Power by Subcutaneous Route.

On the following day and for a total of 14 days, 10 mL/kg were administered to the animals by subcutaneous route in the back of the animal, avoiding the area of the wound.

To that end, the animals were previously homogeneously distributed, according to the body weight, into the following treatment groups:

| Treatment | Dose |
|---|---|
| Diabetic control | — |
| Diabetic animal treated with fondaparinux sodium | 1 mg/kg |
| Diabetic animal treated with bemiparin sodium | 1000 IU Xa/kg |
| Diabetic animal treated with heparin calcium | 600 IU Xa/kg |
| Diabetic animal treated with BP06408-66/28-A | 10 mg/kg |
| Diabetic animal treated with RO-14 | 1000 IU Xa/kg |

The follow-up of the animals was performed up to a period of 21 days (average time necessary for the healing of the wounds in this animal model). The assessment was performed by means of digital photography of the wound and subsequent image analysis.

Measurement of the Wound Area

FIG. 4 shows the evolution of the diabetic control mice with respect to the mice treated with bemiparin sodium. The wound area has been depicted to the right of each animal.

FIG. 5 shows the evolution of the percentage of healing of the wound over time.

The untreated diabetic animals are the ones showing a slower curing rate, since they do not reach 90% healing on day 21, followed by the animals treated with fondaparinux which did not reach complete curing either, which reach 96% on day 21. The animals treated with bemiparin reach complete curing at time 21 days and have healing values of 98% from day 18.

These results indicate that there is no relationship between the anti-Xa activity (determined by the presence of the pentasaccharide responsible for the binding to antithrombin III) of the glycosaminoglycans used and their beneficial effect on healing, since bemiparin sodium is the product with the lowest content of pentasaccharide in its structure (only 1.5% of the total content of monosaccharides corresponds to D-glucuronic acid bound to N-sulfo-3-sulfo-D-glucosamine characteristic of the pentasaccharide) and it has, however, shorter healing times than fondaparinux (pure pentasaccharide, D-glucuronic acid bound to N-sulfo-3-sulfo-D-glucosamine represents 20% of the total content of monosaccharides).

In relation to the areas of the ulcers, when all the products are compared, it is observed how the glycosaminoglycans which have a greater proportion of monosaccharides of the regular region have a beneficial effect in the healing of the wounds. This fact is observed in FIG. 5, where it is seen that non-fractionated heparin as well as bemiparin sodium favor healing, obtaining a percentage above 80% after day 11 of administration.

Macroscopic Evaluation

In the extracted data, considerable macroscopic differences are observed between the groups Non-fractionated heparin calcium, RO-14 and Bemiparin, a different behavior being observed from the fifth day of observation. In this way, it can be seen how the group treated with bemiparin shows a clear difference in the quality of the scar after the fifth day of treatment, a bed covered with granulation tissue being observed in the wound, a fact which does not occur in the control group, and partially in the group treated with fondaparinux.

This differential fact marks the rate in the process and the quality of the healing (as observed in FIG. 5), since granulation tissue is responsible for cell tissue regeneration and healing, in addition to protecting the animal from possible infections.

Furthermore, in the control group it is observed that granulation tissue is not produced (the base of the wound is clear and shiny), and in the group treated with Fondaparinux it is only seen in the edges of the wounds. Therefore, the closure of the wounds of the control diabetic mice and those treated with fondaparinux occurs by the contraction of the edges of the wounds, this process being slower than that occurring by the formation of granulation tissue. Additionally, the wound of the group treated with Bemiparin closes on day 18, whereas in the control group the wound remains open with subsequent risk of infections and of complications.

Histopathological Evaluation

The animals were sacrificed on day 21 of the study and the area of the skin where the wound was caused was stored in formol to perform a histopathological evaluation (hematoxylin-eosin staining).

Each section was given a histological score in the grade 1 to grade V range, where I means uncured wound and V means completely epithelialized wound. The score is based on the degree of cell invasion, the formation of granulation tissue, vascularization and epithelialization.

| Grade | Score | Description |
|---|---|---|
| I | 1-3 | Nil to minimum cell accumulation, absence of granulation tissue or epithelial development. |
| II | 4-6 | Fine and immature granulation tissue dominated by inflammatory cells but with few fibroblasts, capillaries or collagen deposition; minimum epithelial migration. |
| III | 7-9 | Moderately thick granulation tissue. It can vary from being dominated by inflammatory cells to greater presence of fibroblasts and collagen deposition, extensive neovascularization, minimum to moderate epithelial migration. |
| IV | 10-12 | Thick and vascular granulation tissue dominated by fibroblasts and extensive collagen deposition, the epithelium covers the wound partially or completely. |
| V | 13-15 | Area corresponding to the completely epithelialized wound, without having, more or less, traces of the wound. |

The histopathological scores obtained for the different groups are shown in Table 7.

TABLE 7

| Treatment | Score | Grade |
|---|---|---|
| Diabetic control | 6.7 | III |
| Diabetic animal treated with fondaparinux sodium | 7.2 | III |
| Diabetic animal treated with bemiparin sodium | 11.5 | IV |
| Diabetic animal treated with heparin calcium | 8.0 | III |
| Diabetic animal treated with BP06408-66/28-A | 9.0 | III |

The morphological study of the sections corresponding to the skin samples showed the normal evolution of the cicatricial repair process in all the groups. In the treated groups, the granulation tissue is fully formed, bemiparin sodium obtaining the best score, since, in this case, a completely new cell structure by the restitution to the original condition is observed (see FIG. 6 panel C), in which the following results are observed:

A Complete reepithelialization. Little inflammatory infiltrate in dermis. Moderate presence of fibroblasts in dermis. Moderate neovascularization in dermis.

B Complete reepithelialization. Moderate inflammatory infiltrate, polymorphonuclear neutrophils in dermis. Moderate presence of fibroblasts in dermis. Moderate neovascularization in dermis.

C Completely regenerated cell structure.

From the results obtained by the determination of the wound area and the histopathological evaluation, it can be concluded that the best of the products assayed is bemiparin because it is the one having the shortest healing time and the highest tissue quality. Another product which seems to work quite well is the experimental product BP06408-66/28-A. Therefore, it is again demonstrated that a greater factor Xa inhibitory activity is not correlated with a better effect on healing.

Study of the Relationship of the Factor Xa Inhibitory Activity of the Glycosaminoglycan and its Healing Power by Topical Route.

In this case, topical formulations were prepared for the direct administration on the ulcers, the carriers of which formulations are formed by Carbopol, Phenonip®, Span 80, Glycerol and water.

The ulceration and measurement of the area were performed as detailed in the subcutaneous administration assays. On the day after the incision and for a total of 14 days, the assigned treatments, 0.15 ml/animal by topical route in the back of the animal, above the wound, were administered to the animals.

To that end, the animals were previously homogeneously distributed, according to the body weight, into the following treatment groups:

| Treatment | Dose |
|---|---|
| Diabetic control | — |
| Diabetic animal treated with bemiparin | 1000 IU/kg |
| Diabetic animal treated with fondaparinux | 1000 IU/kg |
| Diabetic animal treated with heparin calcium | 1000 IU/kg |

The follow-up of the animals was performed up to a period of 14 days (average time necessary for the healing of the wounds in this animal model). The assessment was performed by means of digital photography of the wound and subsequent image analysis. FIG. 7 shows the overall values of the evolution of the percentage of wound reduction of the treatment groups compared to the control group. As observed in the graph, the best of the wounds was observed with bemiparin, a value of area reduction greater than 60% being obtained at the end of the treatment.

Macroscopic Evaluation

As observed macroscopically, considerable differences are seen in all the groups (control, bemiparin, bondaparinux and non-fractionated heparin calcium (NFH) a different behavior being distinguished after the seventh day of observation.

While in the control group it is observed on the seventh day that no granulation tissue is produced (the base of the wound is clear and shiny), it can be seen in contrast how the treated groups show a clear difference in the quality of the scar on the same day of treatment, a bed covered with granulation tissue being observed in the wound. This differential fact marks the rate in the process and the quality of the healing, since the granulation tissue is responsible for cell tissue regeneration and healing, in addition to protecting the animal from possible infections, as it is very rich in fibroblasts, capillary vessels and collagen.

Histopathological Evaluation.

The animals were sacrificed on the day after the last administration (day 15) and the area where the wound was made was extracted. The rear portion of the area containing the wound was stored in formol for its histological processing (hematoxylin-eosin staining).

The results were based on the score given by the method of Greenhalgh et al. (1990). Each block was given a histological score from 1 to 15, where 1 means uncured wound and 15 means completely epithelialized wound. The score is based on the degree of cell invasion, the formation of granulation tissue, vascularization and epithelialization:

The histopathological scores obtained for the different groups are shown in the table below.

| Treatment | Score | Grade |
|---|---|---|
| Diabetic control | 6.7 | III |
| Diabetic animal treated with bemiparin | 8.7 | III |
| Diabetic animal treated with fondaparinux | 8.6 | III |
| Diabetic animal treated with NFH | 9.4 | IV |

The three treated groups generally obtain a better histological score than the control group, at least two points above the latter. In spite of the fact that the healing in all the groups (control and treated groups) is characterized by the presence of moderately thick granulation tissue, the difference between them is in the greater presence of inflammatory cells, as occurs in the case of the control group, compared to the greater presence of fibroblasts and collagen fiber deposition, as is the case of the treated groups. This indicates that in the case of the control group the healing process is in earlier stages, thus explaining the slower healing rate shown in the studies of wound area reduction. Within the treatments, the skin samples belonging to the groups treated with bemiparin and NFH have a somewhat more evolved cicatricial repair rate, with a more evolved granulation tissue, greater presence of fibroblasts and dermal neovascularization.

The group treated with NFH is different in histological score, being comprised within grade IV, which indicates a higher quality in the healing with respect to the other groups. The granulation tissue formed is thicker and is dominated by fibroblasts, with extensive collagen fiber deposition. The epithelium covers the wound partially or completely.

From the results obtained both by the determination of the wound area and by the histopathological evaluation, it can be concluded that the best products assayed are bemiparin and NFH. Bemiparin has a greater healing rate, whereas in the case of NFH the healing is slower but with higher quality in the tissue formed.

Example 5

Ulceration of the C57BL/KS.Cg-m Lepr$^{Db}$+/+m Mouse, Measurement of the Degree of Healing and Histological Evaluation. Study of the Healing Effect of an NFH and an LMWH in Non-Diabetic Animals. Determination of the Potential Application of Heparins in the Treatment of Chronic Ulcers in Non-Diabetic Patients, by Oral, Subcutaneous and Topical Route The C57BL/KS.Cg-m Lepr$^{db}$+/+m mouse is the non-diabetic analog of the mouse used in the previous example.

On the first day of the assay, the animals were anesthetized (ketamine+xylazine, 100+10 mg/kg, i.m.). The back of the animal was shaved, the area was cleaned with disinfectant and the location of the wound was marked by means of a template to make its position the same in all the animals.

The wound was made by means of a circular incision with a diameter of approximately 1.5 cm, the skin of the mid-dorsal area being removed. A semipermeable dressing was subsequently placed on the wound. 1 mL/animal of physiological serum was administered by i.p. route after the intervention.

Analgesia (paracetamol, 1 mg/mL) was administered in drinking water for the 7 days after the intervention.

The wound area was calculated as the percentage of reduction thereof to evaluate the degree of curing thereof, by means of the standardized formula:

$$\% \text{ curing} = \frac{(A_{baseline} - A_{time})}{(A_{baseline})} \times 100$$

The measurement performed immediately after the intervention or incision was used as the baseline area. On the following day and for a total of 14 days, the assigned treatments were administered to the animals.

Study of the Relationship of the Factor Xa Inhibitory Activity of the Glycosaminoglycan and its Healing Power by Subcutaneous Route.

On the following day and for a total of 14 days, 10 ml/kg were administered to the animals by subcutaneous route in the back of the animal, avoiding the area of the wound.

To that end, the animals were previously homogeneously distributed, according to the body weight, into the following treatment groups:

| Treatment | Dose |
|---|---|
| Non-diabetic control | — |
| Non-diabetic animal treated with bemiparin Na | 1000 IU Xa/kg |
| Non-diabetic animal treated with heparin Ca | 600 IU Xa/kg |
| Non-diabetic animal treated with BP06408-66/28-A | 10 mg/kg |

The follow-up of the animals was performed up to a period of 21 days. The assessment was performed by means of digital photography of the wound and subsequent image analysis.

FIG. 8 shows the evolution of the non-diabetic control mice with respect to the mice treated with heparin calcium. The wound area has been depicted to the right of each animal.

FIG. 9 shows the evolution of the percentage of healing of the wound over time.

The untreated non-diabetic animals reach values of wound reduction greater than 90% after day 14. The treatment with bemiparin sodium does not improve the healing rate. However, the animals treated with heparin calcium do improve with respect to the control, reaching 90% healing on day 11.

Macroscopic Evaluation

The three groups of animals have a normal healing process, the wounds being cured on day 21. However, it seems that in the group of mice treated with heparin calcium the process has sped up since on day 11 the wound is dry and closed, and on day 21 it is covered with hair.

Histopathological Evaluation

The animals were sacrificed on day 21 of the study and the area of the skin where the wound was caused was stored in formol to perform a histopathological evaluation (hematoxylin-eosin staining).

Each section was given a histological score in the grade 1 to grade V range, where I means uncured wound and V means completely epithelialized wound. The score is based on the degree of cell invasion, the formation of granulation tissue, vascularization and epithelialization.

| Grade | Score | Description |
|---|---|---|
| I | 1-3 | Nil to minimum cell accumulation, absence of granulation tissue or epithelial development. |
| II | 4-6 | Fine and immature granulation tissue dominated by inflammatory cells but with few fibroblasts, capillaries or collagen deposition; minimum epithelial migration. |
| III | 7-9 | Moderately thick granulation tissue. It can vary from being dominated by inflammatory cells to greater presence of fibroblasts and collagen deposition, extensive neovascularization, minimum to moderate epithelial migration. |
| IV | 10-12 | Thick and vascular granulation tissue dominated by fibroblasts and extensive collagen deposition, the epithelium covers the wound partially or completely. |
| V | 13-15 | Area corresponding to the completely epithelialized wound, without having, more or less, traces of the wound. |

The histopathological scores obtained for the different groups are shown in Table 8.

TABLE 8

| Treatment | Score | Grade |
|---|---|---|
| Non-diabetic control | 11.7 | IV |
| Non-diabetic animal treated with bemiparin Na | 8 | III |
| Non-diabetic animal treated with heparin calcium | 15 | V |
| Non-diabetic animal treated with BP06408-66/28-A | 12.8 | V |

The morphological study of the sections corresponding to the skin samples showed the normal evolution of the cicatricial repair process in all the groups. In all the treated groups, the granulation tissue is fully formed, obtaining the best score in the treatment with heparin calcium, since, in this case, a completely new cell structure by the restitution to the original condition is observed. In addition, for the case of non-diabetic animals, the score obtained with the sample of the investigational product BP06408-66/28A, which hardly has the presence of the pentasaccharide in its structure, is especially good with a complete cell structure and a very high degree of epithelialization, which again demonstrates that a higher factor Xa inhibitory activity is not necessary for the treatment of chronic ulcers, since it is not correlated with a better effect on healing.

FIG. 10 shows microphotographs of the sections of the wounds after the staining with hematoxylin-eosin: A non-diabetic control. B non-diabetic animal treated with bemiparin sodium, C non-diabetic animal treated with heparin calcium. The results obtained were the following:

A Complete reepithelialization. No alterations are observed.

B Complete reepithelialization. Mild inflammatory infiltrate, polymorphonuclear neutrophils in dermis. Presence of multinuclear giant cells in dermis. Moderate presence of fibroblasts in dermis. Moderate neovascularization in dermis.

C Completely regenerated cell structure.

From the results obtained by the determination of the wound area and the histopathological evaluation, it can be concluded that the treatment with heparin calcium has a beneficial effect on the healing of the non-diabetic animals, shorter healing time and completely regenerated cell structure, followed by the results obtained with the product in investigational phase BP06408-66/28-A. Therefore, the glycosaminoglycans object of the present invention can be used for treating other chronic ulcers different from diabetic foot ulcers.

Without wishing to be bound by the examples described above, due to the results obtained as well as the behavior observed in the animals, it is believed that it is very likely that the present invention will work for other branched or non-branched polysaccharides, such as pentosan polysulfates, beta-glucans, chondroitin sulfates, dermatan sulfates, carrageenans, alginates, arabinoxylans, galactomannans and glucomannans, among others.

The invention claimed is:

1. A method of treating chronic foot ulcer in a diabetic subject having peripheral arterial occlusive disease comprising administering to the subject a daily dose of low molecular weight or very low molecular weight heparin having a plasma half-life ranging from 3 to 6.9 hours, wherein the average daily dose ranges from 5,000-10,000 IU.

2. The method of claim 1, wherein the ratio of plasma half-life and the average daily dose in IU is in the range of 1:800 to 1:3,300.

3. The method of claim 1, wherein:
the average daily dose of the heparin is about 5,000 IU/day when the plasma half-life of the heparin is in the range of 5.2 to 5.4 hours;
the average daily dose of the heparin is about 5,400 IU/day when the plasma half-life of the heparin is in the range of 6.5 and 6.9 hours;
the average daily dose of the heparin is about 8,000 IU/day when the plasma half-life of the heparin is in the range of 4.0 to 4.4 hours;
the average daily dose of the heparin is about 7,600 IU/day, when the plasma half-life of the heparin is 3.7 hours; or
the average daily dose of the heparin is about 10,000 IU/day when the plasma half-life of the heparin is 3.0 hours.

4. The method of claim 1, wherein the heparin is selected from the group consisting of bemiparin, enoxaparin, nadroparin, tinzaparin, RO14, BEMI-99/4, H13-96/5, BP06408-66/27-A, and BP06408-66/28-A.

5. The method of claim 1, wherein the molecular weight of the heparin ranges from 1,728 to 7,500 Daltons.

6. The method of claim 1, wherein the molecular weight of the heparin is less than 6000 daltons.

7. The method of claim 1, wherein the heparin comprises not greater than 25% wt of the disaccharide unit D-glucuronic acid bound to N-sulfo-3-sulfo-D-glucosamine.

8. The method of claim 7, wherein the heparin contains less than 20% wt of the disaccharide unit D-glucuronic acid bound to N-sulfo-3-sulfo-D-glucosamine.

9. The method of claim 7, wherein the heparin contains less than 10% wt of the disaccharide unit D-glucuronic acid bound to N-sulfo-3-sulfo-D-glucosamine.

10. The method of claim 7, wherein the heparin contains less than 5% wt of the disaccharide unit D-glucuronic acid bound to N-sulfo-3-sulfo-D-glucosamine.

11. The method of claim 1, wherein the heparin comprises 25-50% wt of N-sulfo-3-sulfo-D-glucosamine and 3-25% wt of D-glucuronic acid.

12. The method of claim 11, wherein the heparin comprises N-sulfo-D-glucosamine, N-acetyl-D-glucosamine, L-iduronic acid, 2-sulfated L-iduronic acid and D-glucuronic acid.

13. The method of claim 11, wherein the heparin comprises:
25-50% wt of N-sulfo-D-glucosamine, 0-10% wt of N-acetyl-D-glucosamine, 0-35% of L-iduronic acid, 0-50% wt of 2-sulfated L-iduronic acid and 3-25% wt of D-glucuronic acid;
25-50% wt of N-sulfo-D-glucosamine, 0-10% wt of N-acetyl-D-glucosamine, 0-10% of L-iduronic acid, 15-50% wt of 2-sulfated L-iduronic acid and 3-25% wt of D-glucuronic acid; or
25-50% wt of N-sulfo-D-glucosamine, 0.1-8% wt of N-acetyl-D-glucosamine, 0-10% of L-iduronic acid, 15-40% wt of 2-sulfated L-iduronic acid and 3-15% wt of D-glucuronic acid.

14. The method of claim 1, wherein the heparin is administered parenterally, subcutaneously, orally or topically.

15. The method of claim 1, wherein the heparin is used as the sole therapeutic agent.

16. A method of treating chronic foot ulcer in a diabetic subject having peripheral arterial occlusive disease comprising administering to the subject a daily dose of low molecular weight or very low molecular weight heparin having a plasma half-life ranging from 3 to 6.9 hours, wherein the average daily dose ranges from 5,000-10,000 IU, the heparin comprises not greater than 25% wt of the disaccharide unit D-glucuronic acid bound to N-sulfo-3-sulfo-D-glucosamine, and the ratio of plasma half-life and the average daily dose in IU is in the range of 1:800 to 1:3,300.

17. The method of claim 16, wherein:
the average daily dose of the heparin is about 5,000 IU/day when the plasma half-life of the heparin is in the range of 5.2 to 5.4 hours;
the average daily dose of the heparin is about 5,400 IU/day when the plasma half-life of the heparin is in the range of 6.5 and 6.9 hours;
the average daily dose of the heparin is about 8,000 IU/day when the plasma half-life of the heparin is in the range of 4.0 to 4.4 hours;
the average daily dose of the heparin is about 7,600 IU/day, when the plasma half-life of the heparin is 3.7 hours; or
the average daily dose of the heparin is about 10,000 IU/day when the plasma half-life of the heparin is 3.0 hours.

18. The method of claim 17, wherein the heparin comprises 25-50% wt of N-sulfo-3-sulfo-D-glucosamine and 3-25% wt of D-glucuronic acid.

19. The method of claim 17, wherein the heparin comprises 25-50% wt of N-sulfo-D-glucosamine, 0-10% wt of N-acetyl-D-glucosamine, 0-10% of L-iduronic acid, 15-50% wt of 2-sulfated L-iduronic acid and 3-25% wt of D-glucuronic acid.

20. The method of claim 17, wherein the heparin comprises 25-50% wt of N-sulfo-D-glucosamine, 0.1-8% wt of N-acetyl-D-glucosamine, 0-10% of L-iduronic acid, 15-40% wt of 2-sulfated L-iduronic acid and 3-15% wt of D-glucuronic acid.

21. The method of claim 17, wherein the heparin is selected from the group consisting of bemiparin, enoxaparin, nadroparin, tinzaparin, RO14, BEMI-99/4, H13-96/5, BP06408-66/27-A, and BP06408-66/28-A.

22. The method of claim 17, wherein the heparin is administered parenterally, subcutaneously, orally or topically.

23. The method of claim 17, wherein the heparin is used as the sole therapeutic agent.

24. The method of claim 17, wherein the method is a method of healing chronic foot ulcer in a diabetic subject having peripheral arterial occlusive disease.

\* \* \* \* \*